US010046013B2

(12) United States Patent
Sarkar et al.

(10) Patent No.: US 10,046,013 B2
(45) Date of Patent: Aug. 14, 2018

(54) ENGINEERED BACTERIA FOR ORAL DELIVERY OF GLUCOREGULATORY PROTEINS

(75) Inventors: Casim Ali Sarkar, Minneapolis, MN (US); Ting Wun Ng, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 237 days.

(21) Appl. No.: 14/003,596

(22) PCT Filed: Mar. 8, 2012

(86) PCT No.: PCT/US2012/028178
§ 371 (c)(1),
(2), (4) Date: May 19, 2014

(87) PCT Pub. No.: WO2012/122326
PCT Pub. Date: Sep. 13, 2012

(65) Prior Publication Data
US 2014/0242111 A1 Aug. 28, 2014

Related U.S. Application Data

(60) Provisional application No. 61/450,402, filed on Mar. 8, 2011, provisional application No. 61/479,657, filed on Apr. 27, 2011.

(51) Int. Cl.
A61K 39/02 (2006.01)
A61K 35/74 (2015.01)
C07K 14/575 (2006.01)
C07K 14/62 (2006.01)
A61K 38/00 (2006.01)

(52) U.S. Cl.
CPC .......... A61K 35/74 (2013.01); C07K 14/5759 (2013.01); C07K 14/62 (2013.01); A61K 38/00 (2013.01)

(58) Field of Classification Search
None
See application file for complete search history.

(56) References Cited

U.S. PATENT DOCUMENTS 5,756,461 A * 5/1998 Stephens ............ A61K 38/2264 514/5.8
2005/0075298 A1 4/2005 Chen et al.
2008/0219960 A1 9/2008 Nierop Groot
2009/0286723 A1 11/2009 Levy et al.

FOREIGN PATENT DOCUMENTS

WO 12/28178 3/2012

OTHER PUBLICATIONS

The potential osteogenic effects of systemic leptin and insulin administration in streptozotocin-induced diabetic female rats GAD, H.I. Saudi Medical Journal, vol. 28, No. 8, 2007 Abstract only.*
Balcazar et al., "Changes in intestinal microbiota and humoral immune response following probiotic administration in brown trout (Salmo trutta)" 2007, Br J Nutr 97(3):522-7.
Bermudez-Humaran et al., "Controlled intra- or extracellular production of staphylococcal nuclease and ovine omega interferon in Lactococcus lactis" 2003, FEMS Microbiol Lett 224(2):307-13.
Braat et al., "A Phase I Trial With Transgenic Bacteria Expressing Interleukin-10 in Crohn's Disease" 2006, Clin Gastroenterol Hepatol 4(6):754-9.
Charman et al., "Physicochemical and Physiological Mechanisms for the Effects of Food on Drug Absorption: The Role of Lipids and pH" 1997, J Pharm Sci 86(3):269-82.
Chen et al., "Artificial cell-cell communication in yeast Saccharomyces cerevisiae using signaling elements from Arabidopsis thaliana" 2005, Nat Biotechnol 23:1551-1555.
De Ruyter et al., "Controlled Gene Expression Systems for Lactococcus lactis with the Food-Grade Inducer Nisin" 1996, Appl Environ Microbiol 62:3662-3667.
De Ruyter et al., "Functional Analysis of Promoters in the Nisin Gene Cluster of Lactococcus lactis" 1996, J Bacteriol 178:3434-3439.
Hua et al., "Mechanism of Insulin Chain Combination" 2002, Journal of Biological Chemistry 277(45):43443-53.
Klijn et al., "Genetic Marking of Lactococcus lactis Shows Its Survival in the Human Gastrointestinal Tract" 1995, Appl Environ Microbiol 61(7):2771-4.
Le Loir et al., "Signal Peptide and Propeptide Optimization for Heterologous Protein Secretion in Lactococcus lactis" 2001, Appl Environ Microbiol 67(9):4119-27.
McAuliffe et al., "Lantibiotics: structure, biosynthesis and mode of action" 2001, FEMS Microbiol Rev 25(3):285-308.
Morishita et al., "Is the oral route possible for peptide and protein drug delivery?" 2006, Drug Discov Today 11:905-10.
Muller G., "Oral Delivery of Protein Drugs: Driver for Personalized Medicine?" 2010, Curr Issues Mol Biol 13(1):13-24.
Nouaille et al., "Heterolgous protein production and delivery systems for Lactococcus lactis" 2003, Genet Mol Res 2(1):102-11.
Palani et al., "Integrating Extrinsic and Intrinsic Cues into a Minimal Model of Lineage Commitment for Hematopoietic Progenitors" 2008, Biophys J 95:1575-1589.
Palani et al., "Positive Receptor Feedback during Lineage Commitment Can Generate Ultrasensitivity to Ligand and Confer Robustness to a Bistable Switch" 2009, PLoS Comp Biol 5, e1000518.
Steidler et al., "Treatment of Murine Colitis by Lactococcus lactis Secreting Interleukin-10" 2000, Science 289 (5483): 1352-5.
Steidler et al., "Biological containment of genetically modified Lactococcus lactis for intestinal delivery of human interleukin 10" 2003, Nat Biotechnol 21(7):785-9.
Van Asseldonk et al., "Cloning of usp45, a gene encoding a secreted protein from Lactococcus lactis subsp. Lactis MG1363" 1990, Gene 95:155-160.
Weiss, "Proinsulin and the Genetics of Diabetes Mellitus" 2009, Journal of Biological Chemistry 284(29):19159-63.

(Continued)

Primary Examiner — Ja'Na Hines
Assistant Examiner — Khatol Shahnan Shah
(74) Attorney, Agent, or Firm — Riverside Law LLP

(57) ABSTRACT

Disclosed is an oral delivery system that overcomes major barriers encountered in the gastrointestinal tract, particularly rapid proteolytic degradation and low intestinal permeability. Provided is a method for oral delivery of an engineered microorganism to a mammal where the microorganism produces a macromolecule having a desired bioavailability outcome.

4 Claims, 8 Drawing Sheets

(56) References Cited

OTHER PUBLICATIONS

Wells et al., "*Mucosal delivery of therapeutic and prophylactic molecules using lactic acid bacteria*" 2008, Nat Rev Microbiol 6(5):349-62.
Zhang et al., "*Crystal structure of the obese protein leptim-E100*" 1997, Nature 387:206-209.
Mierau et al., "10 years of the nisin-controlled gene expression system (NICE) in Lactococcus lactis," 2005, *Appl Microbiol Biotechnol,* 68(6):705-17.
Müller, "Oral Delivery of Protein Drugs: Driver for Personalized Medicine?," Curr. Issues Mol. Biol., 13:13-24.
Khafagy et al., "Current challenges in non-invasive insulin delivery systems: A comparative review," Advanced Drug.Delivery Reviews 59 (2007) 1521-1546.

\* cited by examiner

A.

B.

SEQUENCE LISTING

<160> NUMBER OF SEQ ID NOS: 19

<210> SEQ ID NO 1
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 1
tccggagttt acgctttcgt taaccagcac                                     30

<210> SEQ ID NO 2
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 2
cactcaaaga attcatgttc gttaaccagc ac                                  32

<210> SEQ ID NO 3
<211> LENGTH: 40
<212> TYPE: DNA
<213> ORGANISM: Artificial Sequence
<220> FEATURE:
<223> OTHER INFORMATION: Chemically Synthesized

<400> SEQUENCE: 3
tggtggtgat ggtgggatcc tctgttgcag tagttttcca                          40

<210> SEQ ID NO 4
<211> LENGTH: 96
<212> TYPE: DNA
<213> ORGANISM: Artificial Sequence
<220> FEATURE:
<223> OTHER INFORMATION: Chemically Synthesized

<400> SEQUENCE: 4
gcactcaaag aattcatgaa aaaaagatt atctcagcta ttttaatgtc tacagtgata    60
ctttctgctg cagccccgtt gtccggagtt tacgct                              96

```
<210> SEQ ID NO 5
<211> LENGTH: 38
<212> TYPE: DNA
<213> ORGANISM: Artificial Sequence
<220> FEATURE:
<223> OTHER INFORMATION: Chemically Synthesized

<400> SEQUENCE: 5
ccccgttgtc cggagtttac gctttcgtta accagcac                              38

<210> SEQ ID NO 6
<211> LENGTH: 36
<212> TYPE: DNA
<213> ORGANISM: Artificial Sequence
<220> FEATURE:
<223> OTHER INFORMATION: Chemically Synthesized

<400> SEQUENCE: 6
gaactagtgg tacctcatta gttgcagtag ttttcc                                36

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
tacagctcca agatctagtc                                                  20

<210> SEQ ID NO 8
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 8
catgaattct ttgagtgcct ccttata                                          27

<210> SEQ ID NO 9
<211> LENGTH: 39
<212> TYPE: DNA
<213> ORGANISM: Artificial Sequence
<220> FEATURE:
<223> OTHER INFORMATION: Chemically Synthesized

<400> SEQUENCE: 9
gaactagtgg tacctcatta atgatggtgg tgatggtgg                             39

<210> SEQ ID NO 10
<211> LENGTH: 200
<212> TYPE: DNA
<213> ORGANISM: Artificial Sequence
<220> FEATURE:
<223> OTHER INFORMATION: Chemically Synthesized

<400> SEQUENCE: 10
atatatccat gggcttcgtt aaccagcacc tgtgcggttc tgacctggtt gaagctctgt      60
acctggtttg cggtgaacgt ggtttcttct acaccgaccc gaccggtggt ggtccgcgtc     120
gtggtatcgt tgaacagtgc tgccactcta tctgctctct gtaccagctg gaaaactact     180
gcaacgaatt cggatctggt                                                 200
```

<210> SEQ ID NO 11
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 11
agaaggagat atatccatgg                    20

<210> SEQ ID NO 12
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 12
tggccaccag atccgaattc                    20

<210> SEQ ID NO 13
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 13

Gly Gly Ser Gly
1

<210> SEQ ID NO 14
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 14

Gly Ala Gly Gly Ser Gly Gly Ser
1               5

<210> SEQ ID NO 15
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 15

Gly Gly Gly Ser Gly Gly Ala Gly Gly Ser Gly
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 16

Ala Glu Ala Ala Ala Lys Glu Ala Ala Ala Lys Ala
1               5                   10

```
<210> SEQ ID NO 17
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 17

Gly Ser Pro Asp Gly Asp Ile Asp Gly Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 18

Gly Ser Leu Val Pro Arg Gly Ser Gly Ser
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 19

Gly Gly Gly Pro Arg Arg
1               5
```

ENGINEERED BACTERIA FOR ORAL DELIVERY OF GLUCOREGULATORY PROTEINS

CROSS-REFERENCE TO RELATED APPLICATIONS

This application is the U.S. national phase application filed under 35 U.S.C. § 371 claiming benefit to International Patent Application No. PCT/US2012/028178, filed on Mar. 8, 2012, which is entitled to priority under 35 U.S.C. § 119(e) to U.S. Provisional Patent Application No. 61/450,402, filed on Mar. 8, 2011 and U.S. Provisional Patent Application No. 61/479,657, filed on Apr. 27, 2011, the contents of each of which are incorporated by reference herein in their entireties.

BACKGROUND OF THE INVENTION

Oral administration is one of the most convenient ways of delivering drugs, but therapeutic proteins often must be administered by an invasive method, such as intravenous or subcutaneous injection (Morishita et al., 2006, Drug Discov Today 11:905-10). Oral delivery of protein drugs is not generally feasible due to poor stability during passage through the gastrointestinal tract and low permeability across the intestinal wall, resulting in insufficient bioavailability. To increase oral bioavailability of proteins, various encapsulation strategies have been developed to protect the polypeptides from enzymatic digestion (Muller G., 2010, Curr Issues Mol Biol 13(1):13-24), but most have encountered roadblocks that prevent them from advancing to a clinical setting (Khafagy et al., 2007, Adv Drug Deliv Rev 59(15):1521-46).

L. lactis is a gram-positive bacterium widely used in the food industry for production of fermented products such as buttermilk and cheese and is therefore routinely consumed in these foods. L. lactis has a safe association with humans and has been proposed for use as a probiotic (Balcazar et al., 2007, Br J Nutr 97(3):522-7). There has been increasing interest in the use of L. lactis as a mucosal delivery vehicle because it can survive passage through the stomach acid and contact with bile (Klijn et al., 1995, Appl Environ Microbiol 61(7):2771-4) and it can be engineered to express and secrete targeting molecules and adjuvants (Nouaille et al., 2003, Genet Mol Res 2(1):102-11). Antigens and DNA have been introduced for mucosal vaccine delivery, single-chain variable fragments (scFvs) for anti-infectives, and allergens for allergy prevention (Wells et al., 2008, Nat Rev Microbiol 6(5):349-62). To address potential safety concerns of using live L. lactis in humans, the thymidylate synthase gene can be removed from the host genome, rendering the auxotrophic bacteria dependent on thymidine or thymine for survival and thus biologically contained (Steidler et al., 2003, Nat Biotechnol 21(7):785-9). In addition, since the recombinant protein is still locally produced when the bacteria reach the intestine, proteolytic degradation is attenuated. A study involving the use of interleukin-10-secreting L. lactis to treat Crohn's disease has passed phase I clinical trials, supporting the notion that this live microorganism is a viable platform for oral protein delivery (Braat et al., 2006, Clin Gastroenterol Hepatol 4(6):754-9; Steidler et al., 2000, Science 289 (5483): 1352-5).

Oral administration of a number of classes of agents is limited by poor absorption, degradation by gastric and intestinal enzymes or instability of the agent in aqueous solutions generally and in the low pH environment of the stomach in particular. This is especially problematic for delivery of protein or peptide bioactive agents, which at present are primarily administered parenterally. However, other types of bioactive agents may exhibit similar problems when orally administered.

Oral delivery of insulin to diabetic patients is highly desirable because it would be noninvasive and more closely mimic normal physiology, but this route of administration typically results in low bioavailability due to low pH, enzymatic degradation along the gastrointestinal tract, and poor absorption. Thus, there is a need in field to develop improved oral delivery systems having a desirable bioavailability outcome. The present invention satisfies this need.

SUMMARY OF THE INVENTION

The present invention provides a genetically modified microorganism for oral delivery of a macromolecule to a mammal, wherein the microorganism produces the macromolecule in the intestine of the mammal. In one embodiment, the mammal is a human.

In one embodiment, the microorganism is a gram positive bacterium.

In one embodiment, the microorganism is Lactococcus lactis.

In one embodiment, the Lactococcus lactis is the NZ9000 strain. Preferably, the microorganism has been engineered for nisin-inducible expression and secretion of a therapeutic protein.

In one embodiment, the therapeutic protein is a glucoregulatory protein.

In one embodiment, the therapeutic protein is a fusion protein comprising insulin and leptin.

The present invention also provides a method of oral delivery of insulin to a mammal, the method comprising orally administering a genetically modified microorganism to the mammal, wherein the microorganism produces and secretes insulin in the intestine of the mammal. In one embodiment, the mammal is a human.

In one embodiment, the insulin secreted by the microorganism is able to cross the intestinal lumen.

The invention also provides a method of immunizing a mammal. In one embodiment, the method comprises orally administering an effective amount of a genetically modified microorganism to the mammal, wherein the microorganism produces and secretes a macromolecule in the intestine of the mammal. Preferably, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 8A and 8B, is a series of images depicting the effect of nisin concentration and induction time on growth rate. Various nisin concentrations (♦: no nisin; ■: 0.001 ng/ml; ▲: 0.01 ng/ml; ●: 0.1 ng/ml; ◇: 0.5 ng/ml; □: 1 ng/ml; Δ: 5 ng/ml; ○: 10 ng/ml) were added at (A) 1 hr and (B) 2.5 hr after 1:25 dilution of an overnight culture of NZ9000(pNZPnisA:uspSCI-57his). Cultures were grown statically at 30° C. for a total of 7 hr. Growth was determined by measuring the optical density at 600 nm over time.

DETAILED DESCRIPTION OF THE INVENTION

Figure 1:
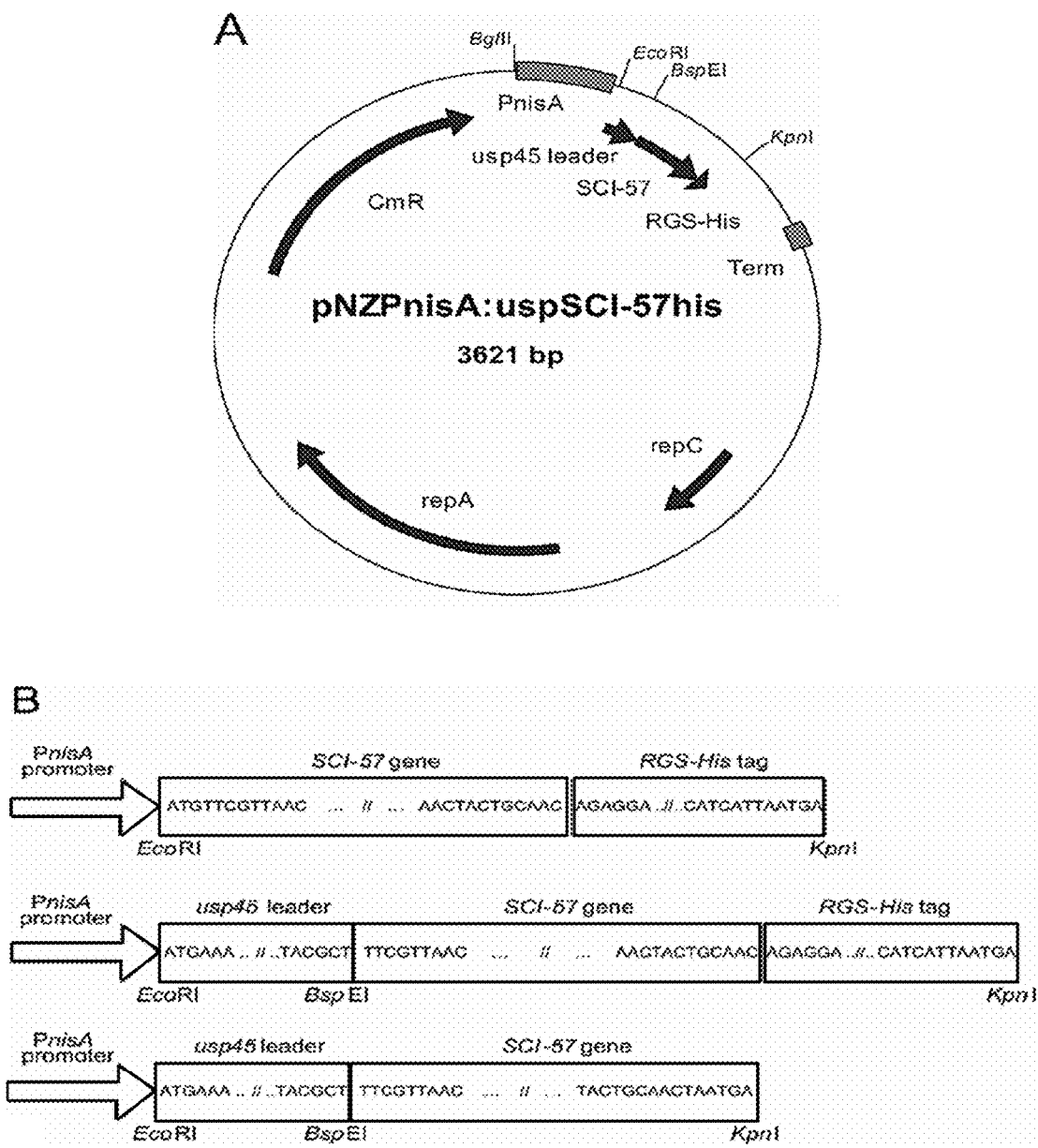
FIG. 1 is a schematic representation of the various constructs used in this study. (A) Representative map of pNZPnisA:uspSCI-57his showing promoter PnisA, usp45 leader signal, SCI-57 gene, and RGS-His tag in the modified pNZ8048 backbone. (B) Partial DNA sequences of the gene constructs inserted into the modified pNZ8048 backbone. From top to bottom: pNZPnisA:SCI-57his, pNZPnisA:uspSCI-57his and pNZPnisA:uspSCI-57. For pNZPnisA:SCI-57his and pNZPnisA:uspSCI-57his, gene constructs were generated by assembly PCR, digested with KpnI and BglII, and ligated into the similarly digested pNZPnisA:CYTOLLO vector. For pNZPnisA:uspSCI-57, the assembly PCR product was digested by KpnI and BspEI and ligated into a similarly digested pNZPnisA:uspSCI-57his vector. All plasmids were maintained in *E. coli* EC1000, and subsequently transformed into electrocompetent *L. lactis* NZ9000.

The invention relates to an oral delivery system that overcomes major barriers encountered in the gastrointestinal tract, particularly rapid proteolytic degradation and low intestinal permeability.

The present invention relates generally to a microorganism engineered to express and secrete a macromolecule, for example a therapeutic protein, in a mammal. In one embodiment, the engineered microorganism is a food-grade bacterium. Therefore, the invention provides a method of orally administering an engineered microorganism as a means to deliver a macromolecule to the gastrointestinal tract of a mammal. In one embodiment, the administered microorganism expresses and secretes the desired agent in the gastrointestinal tract of the mammal where the agent has a desired pharmacokinetic effect.

In one embodiment, the microorganism is engineered to locally produce the desired macromolecule in the intestine. In this manner, the invention provides a method of minimizing the adverse effects of harsh pH and digestive enzymes associated with the macromolecule being in the gastrointestinal tract. Preferably, the macromolecule is able to cross the intestinal lumen. Therefore, in one embodiment, the engineered microorganism can be orally administered to a mammal for the purpose of systemic delivery of a desired macromolecule. Preferably, the desired macromolecule is a glucoregulatory protein.

In another embodiment, the macromolecule is a therapeutic agent. Preferably, the therapeutic agent is bioactive insulin and analogs thereof. In another embodiment, the therapeutic agent is leptin and analogs thereof. In yet another embodiment, the therapeutic agent is a fusion protein comprising insulin and leptin or analogs of either or both insulin and leptin.

In another embodiment, the present invention provides an engineered microorganism for oral use which safely delivers a macromolecule such as a growth hormone into the intestine, whereby the molecule is adsorbed into the body.

In one embodiment, the invention provides a genetically modified microorganism for the intestinal delivery of a desired macromolecule. In one embodiment, the invention provides an efficient protein-based treatment given by the oral route. In another embodiment, the invention provides an improved oral delivery system of a bioactive agent, such as a vaccine.

The invention relates to the discovery that a microorganism genetically modified to produce a bioactive molecule can be used to deliver the bioactive molecule orally to a subject in need thereof. One example of a microorganism useful for the compositions and methods of the invention is *Lactococcus lactis*.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, to "alleviate" a disease means reducing the frequency or severity of at least one sign or symptom of a disease or disorder.

The term "biologically active" as used herein in relation to the heterologous polypeptide expressed in the host cell denotes that the polypeptide is produced in an appropriate conformation for obtaining biological activity, rather than a misfolded, aggregated and insoluble form which requires special denaturation and renaturation measures to achieve an appropriate conformation to any substantial extent.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

By the term "effective amount", as used herein, is meant an amount that when administered to a mammal, causes a detectable level of a biological response compared to the biological response detected in the absence of the administration. Biological responses can be readily assessed by a plethora of art-recognized methods.

The skilled artisan would understand that the amount of a compound or composition administered herein varies and can be readily determined based on a number of factors such as the disease or condition being treated, the age and health and physical condition of the mammal being treated, the severity of the disease, the particular compound being administered, and the like.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

As used herein, the term "fragment" as applied to a nucleic acid, may ordinarily be at least about 18 nucleotides in length, preferably, at least about 24 nucleotides, more typically, from about 24 to about 50 nucleotides, preferably, at least about 50 to about 100 nucleotides, even more preferably, at least about 100 nucleotides to about 200 nucleotides, yet even more preferably, at least about 200 to about 300, even more preferably, at least about 300 nucleotides to about 400 nucleotides, yet even more preferably, at least about 400 to about 500, and most preferably, the nucleic acid fragment will be greater than about 500 nucleotides in length.

As applied to a protein, a "fragment" of a protein is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "microorganism" as used herein refers to a cell, a bacterium, a fungus, a virus, an algae, and a protozoa. A preferred microorganism can be genetically manipulated to produce a desired polypeptide(s).

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "recombinant cell" is a cell that comprises a transgene. Such a cell may be a eukaryotic cell or a prokaryotic cell.

By the term "exogenous nucleic acid" is meant that the nucleic acid has been introduced into a cell or an animal using technology which has been developed for the purpose of facilitating the introduction of a nucleic acid into a cell or an animal.

As used herein, the term "transgenic mammal" means a mammal, the germ cells of which comprise an exogenous nucleic acid.

As used herein, to "treat" means reducing the frequency and/or severity of symptoms of a disease, or disorder, experienced by a patient.

The term "vaccine" as used herein is defined as a material used to provoke an immune response after administration of the material to a mammal.

By the term "vector" as used herein, is meant any plasmid or virus encoding an exogenous nucleic acid. In addition, the term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of a nucleic acid that encodes a protein of the invention, to the patient, or the vector may be a non-viral vector which is suitable for the same purpose.

A "therapeutic" treatment is a treatment administered to a patient who exhibits signs of pathology for the purpose of diminishing or eliminating at least one sign or symptom, and/or decreasing or diminishing the frequency, duration and intensity of at least one sign or symptom of a disease or disorder.

To "treat" a disease as the term is used herein, means to reduce the frequency and/or severity of at least one sign or symptom of a disease or disorder experienced by an animal.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to an oral delivery system comprising a live microorganism engineered to express and secrete a desired macromolecule. In one embodiment, the microorganism is a food-grade microorganism such as *Lactococcus lactis*. The food-grade microorganism can be engineered to express and secrete a desired macromolecule such as a glucoregulatory protein. For example, the glucoregulatory protein can include but is not limited to insulin, leptin, and the like. The engineered microorganism enables oral delivery of the desired macromolecule having desired pharmacokinetics in the recipient mammal.

In one embodiment, the use of the engineered food-grade microorganism of the invention overcomes major barriers encountered in the gastrointestinal tract associated with oral administration of a therapeutic agent. For example, administering an agent orally using prior art methods exposes the agent to harsh environmental conditions that result in very low bioavailability. The present invention overcomes this problem by having the food-grade ingestible bacterium locally produce the desired macromolecule in the intestine, thereby minimizing the adverse effects of harsh pH and digestive enzymes on the macromolecule in the gastrointestinal tract.

In one embodiment, macromolecule secreted from the engineered microorganism is able to cross the intestinal membrane thereby allowing for the macromolecule to be present systemically in the mammal. In one embodiment, the microorganism can be engineered to secrete a macromolecule where the macromolecule comprises a linker that is cleavable. In another embodiment, the microorganism can be engineered to secrete a macromolecule where the macromolecule is stable in the bloodstream.

Composition

Any microorganism capable of expressing a desired macromolecule may be used as a delivery vehicle in accordance with the present invention. Such microorganisms include but are not limited to bacteria, viruses, fungi (including yeast), algae, and protozoa. Generally, microorganisms are single cell, single spore or single virion organisms. Additionally, included within the scope of the present invention are cells from multi-cellular organisms which have been modified to produce a polypeptide of interest. Microorganisms that can be genetically manipulated to produce a desired polypeptide are preferred. Genetic manipulation includes mutation of the host genome, insertion of genetic material into the host genome, deletion of genetic material of the host genome, transformation of the host with extrachromosomal genetic material, transformation with linear plasmids, transformation with circular plasmids, insertion of genetic material into the host (e.g., injection of mRNA), insertion of transposons, and chemical modification of genetic material. Methods for constructing nucleic acids (including an expressible gene), and introducing such nucleic acids into an expression system to express the encoded protein are well established in the art (Sambrook et al., Molecular Cloning: A Laboratory Manual, 3$^{rd}$ Ed., Cold Spring Harbor Laboratory Press, Cold Spring Harbor, N.Y., 2001, incorporated herein by reference).

Use of microorganisms such as bacteria and yeast for delivery of a desired macromolecule in accordance with the present invention offers many advantages over delivery of the same macromolecule that is not expressed by the microorganisms of the present invention.

In a preferred embodiment, bacteria are used as protein delivery microorganisms. Generally, bacteria are classified as gram-negative or gram-positive depending on the structure of the cell walls. Those skilled in the art are capable of identifying gram-negative and gram-positive bacteria which may be used to express proteins in accordance with the present invention. Non-limiting examples of genera and species of gram-negative bacteria include *Escherichia coli, Vibro cholera, Salmonella, Listeria, Legionella, Shigella, Yersenia, Citrobacter, Enterobacter, Klebsiella, Morganella, Proteus, Providencia, Serratia, Plesiomonas, Aeromonas*. Non-limiting examples of genera and species of gram positive bacteria which may be used in the present invention include *Bacillus subtilis, Sporolactobacillus, Clostridium, Arthrobacter, Micrococcus, Mycobacterium, Peptococcus, Peptostreptococcus,* and *Lactococcus*.

Gram-positive bacteria have also been studied as delivery vehicles for proteins to modulate an immune response in a subject. WO 97/14806 describes the use of *Lactococcus* to deliver polypeptides into a body to enhance the immune response to the polypeptides. For example, the microorganism of the invention such as *Lactococcus lactis* can be used as a delivery vehicle in the present invention. In addition, *Lactococcus lactis* can be used as a delivery vehicle for production of antigens for use as a live vaccine against infectious organisms. *Lactococcus lactis* can further be used to express and secrete a desired polypeptide in the recipient mammal.

In one embodiment, the Gram-positive bacterial strain is preferably a *Lactococcus* species, and more preferably, a *Lactococcus lactis*. *L. lactis*, is a Gram positive food grade organism which is believed to be totally harmless. It is a non-colonizing micro-organism.

Other Gram-positive bacterial strains to be used for the purpose of the current invention are *Bacillus subtilis, Streptococcus gordonii, Staphylococcus xylosus,* or a *Lactobacillus* species, such as *L. bulgaricus, L. salivarius, L. casey, L. helveticus, L. delbrueckii* or *L. plantarum*.

Microorganisms of the present invention may be administered to a subject as live or dead microorganism. Preferably if the microorganism is administered as a live microorganism, it is non-pathogenic or is an attenuated pathogenic microorganism. For applications of the invention where live microorganisms are administered to individuals, preferably the microorganisms are attenuated and/or are administered in suitable encapsulation materials and/or as pharmaceutical compositions as vaccines to decrease an individual's immune response to the microorganism. Generally, attenuation involves genetically modifying the infectious pathogenic microorganism to reduce or eliminate the infectious ability of the microorganism. Preferably, the microorganism is attenuated such that an individual inoculated with the microorganism does not suffer any cytotoxic effects from the presence of the microorganism. Particularly preferred attenuated microorganisms are infectious intracellular pathogens which are phagocytosed by antigen-present In one embodiment, the invention provides a *Lactococcus lactis* engineered to express a bioactive insulin analog, SCI-57, which contains four substitutions in the A and B chains of insulin and a 6-residue linker (GGGPRR; SEQ ID NO: 19) connecting the A and B chains, resulting in a single polypeptide which is 57 amino acids in length (Hua et al., 2008, Journal of Biological Chemistry 283(21):14703-16). One of the four substitutions in the A and B chains insulin is present in Novalog® and another is present in Humalog®, both of which rapid-acting insulin analogs already in clinical use by injection. SCI-57 resembles the folding and biological activity of wild-type insulin. SCI-57 also has enhanced thermodynamic stability and reduced aggregation, and allows for simpler single-chain synthesis, making it an attractive insulin analog for oral delivery (Hua et al., 2008, Journal of Biological Chemistry 283(21):14703-16; Rajpal et al., 2009, Mol Endocrinol 23(5):679-88).

In one embodiment, the invention provides compositions and methods for oral delivery of a bioactive glucoregulatory protein such as insulin, leptin, and the like. For example, oral delivery of insulin molecule to a subject in need thereof has the benefits of easy administration and improved compliance. Oral delivery of a bioactive insulin molecule also more accurately imitates normal physiological delivery. After absorption in the intestine, orally delivered insulin reaches the portal system, more closely approximating what occurs in a non-diabetic individual (Gordon et al., 2002, Diabetes Metab Res Rev 18 Suppl 1:S29-37). Insulin is normally secreted by pancreatic β-cells in the form of a single-chain precursor, proinsulin, which is subsequently cleaved into separate A (21 residues) and B (30 residues) chains connected by three disulfide bonds (Hua, 2010, Cell 1(6):537-551).

In some embodiments, the insulin molecule of the invention, such as SCI-57, can be inducibly expressed in a microorganism. In some embodiments, the microorganism is *L. lactis*. In preferred embodiments, the *L. lactis* microorganism is the strain NZ9000.

In certain embodiments, the inducible expression is accomplished using the NICE system. The NICE system is on a two-component signaling system involved in the biosynthesis of the bacteriocin nisin (Mierau et al., 2005, Appl Microbiol Biotechnol 68(6):705-17). In the NICE system, upon nisin binding, NisK, a histidine kinase, autophosphorylates and transfers its phosphate group to NisR, which when activated induces transcription of a gene of interest under the control of promoter PnisA (de Ruyter et al., 1996, Appl Environ Microbiol 62(10):3662-7). Linear dose-response curves have been reported for the NICE system.

In some embodiments of the instant invention, the microorganism, such as *L. lactis*, upon nisin induction, can secrete SCI-57 when the gene is fused to the usp45 secretion signal (van Asseldonk et al., 1990, Gene 95(1):155-60). In various embodiments, the bacterial growth rate depends on the timing of nisin induction.

The oral delivery system of the invention is applicable to any protein, polypeptide or peptide drug candidate. For example, the invention includes oral delivery of a protein including but not limited to, insulin, human growth hormone, calcitonin (e.g., salmon calcitonin), an interferon such as an alpha-, beta-, or gamma-interferon, glucagon, gonado-tropin-releasing hormone, enkephalins, vaccines, enzymes, hormone analogs, and enzyme inhibitors. Preferably, the polypeptide is insulin. In one preferred embodiment, the insulin is human recombinant insulin. In another embodiment, the protein is a fusion protein comprising insulin and leptin.

Other bioactive agents to be delivered by oral administration using the claimed methods and compositions may include, but are not limited to, drugs, pharmaceuticals, toxins, anti-cancer agents, anti-inflammatory agents, antibiotics, antifungals, antiviral agents, anti-parasitic agents, vaccines, adjuvants, antigens, hormones, growth factors, cytokines, chemokines, immunomodulators, interferons, interleukins, hematopoietic factors, coagulation factors, anti-angiogenic factors, pro-apoptosis factors, neurotransmitters, neuromodulators, enzymes, agonists, antagonists, antibodies, antibody fragments, fusion proteins, proteins, polypeptides, peptides, nucleic acids, lipids, polysaccharides, carbohydrates or steroids. In certain preferred embodiments, the bioactive agent may be a protein or peptide based agent.

The present invention also provides for analogs of the desired proteins or peptides. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Method

The present invention provides for a method of using a genetically modified microorganism such as *Lactococcus lactis* as an oral delivery system to express a desired macromolecule in a subject.

Accordingly, the invention includes any expression system known in the art or disclosed herein for production of proteins of interest, such as expression in a baculovirus system, a yeast expression system, or a mammalian cell system or a bacterial system, such as, but not limited to, *L. lactis*. Proteins of the invention which are generated by synthetic methods are also included in the invention.

The skilled artisan, based upon the disclosure provided herein, would appreciate that the nucleic acids encoding the proteins of the invention can be expressed alone or in combination with other proteins either in one or separate recombinant cells. Where the proteins are expressed in the same recombinant cell, the exogenous nucleic acids encoding the proteins can be ligated together in either of two configurations. In the first configuration, a plasmid, or other suitable vector, is generated having the following elements: a promoter/regulatory sequence for expression of the first protein, which promoter is operably linked to and positioned upstream of a nucleic acid sequence encoding the first protein, and a promoter for expression of the second protein, which is positioned upstream of a nucleic acid encoding the second protein. The plasmid therefore encodes both proteins on the same contiguous nucleic acid molecule wherein expression of each protein is under the control of an individual promoter/regulatory sequence, preferably, but not necessarily, the same promoter sequence. Both proteins are expressed individually from this plasmid, or other vector, in a cell and form complex therein which is secreted from the cells as described herein.

Alternatively, a plasmid can be generated which has the following elements: a single a promoter/regulatory sequence which is positioned upstream of a nucleic acid encoding a first protein and a sequence encoding a second protein, the sequences encoding the proteins of interest being separated by a nucleic acid sequence encoding a cleavage site for a protease. In this plasmid, the protein-coding sequences can be positioned in the plasmid, or other vector, in either orientation with respect to each other, such that either one of them is juxtaposed to the promoter sequence. DNA encoding the protease cleavage site, which is positioned between the sequences encoding the proteins may be any DNA known to encode a length of amino acids which are cleaved by any protease which is present in a majority of cells and which is particularly present in cells into which the DNA of the invention is introduced. The proteins expressed by this plasmid, or other vector, are expressed as a single contiguous protein comprising the amino acid sequences of each protein fused together and comprising an intervening protease cleavage site. Subsequent cleavage of the fused protein by the appropriate protease generates individual polypeptides to form a composition and/or subunit vaccine as described elsewhere herein.

The isolated nucleic acid of the invention is not limited to a plasmid based nucleic acid, but rather may include any form of nucleic acid which encodes a protein of the invention as exemplified herein in the case of a plasmid DNA used in a baculovirus/insect cell expression system, but not limited in any way to this, or any other, expression method. Thus, the isolated DNA of the invention can include a viral vector, a non-viral vector, or a plasmid DNA, among others.

The promoter/regulatory sequence which is used to drive expression of a protein of the invention in either type of configuration can be any constitutive promoter which drives expression of these proteins in cells. Such promoters therefore include, but are not limited to, the cytomegalovirus immediate early promoter/regulatory sequence, the SV40 early promoter/enhancer sequence, the Rous sarcoma virus promoter/enhancer, a baculovirus expression sequence, and any other suitable promoter which is available in the art for constitutive expression of high levels of proteins in cells.

When the isolated DNA of the invention is used to generate large quantities of the proteins of the invention, cells are transfected with the DNA using the methodology disclosed herein or any other available transfection methodology, the protein of interest is expressed and is recovered from the cells as described herein.

The skilled artisan would understand that the nucleic acids of the invention encompass an RNA or a DNA sequence encoding a protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art. Procedures for the introduction of amino acid changes in a protein or polypeptide by altering the DNA sequence encoding the polypeptide are well known in the art and are also described in these, and other, treatises.

In the context of an expression vector, the vector can be readily introduced into a host cell, e.g., mammalian, bacterial, yeast or insect cell by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Vaccine

In one embodiment, the method comprises an oral dosing regimen which can be easily administered to both human and animal populations. In another embodiment, the method has the ability to generate a mucosal immune response.

The present invention provides a method of inducing an immune response to an antigen, comprising the step of administering to an animal or human genetically modified microorganism of the invention expressing the desired antigen. The genetically modified microorganism of the present invention is capable of inducing an immune response when administered to a subject. The immune response induced by the microorganism of the present invention may include, but is not limited to, a humoral immune response and a mucosal immune response. For example, the microorganism of the present invention is capable of inducing a systemic IgG response and a mucosal IgA response.

In one embodiment, the genetically modified microorganism of the present invention is capable of inducing a protective immune response, i.e. an immune response that can protect the subject from a lethal challenge by a pathogen (such as a virus or bacterium).

In one embodiment, the microorganism of the present invention is genetically modified to express one or more antigens. In an embodiment, the antigen is heterologous with respect to the mammal Examples of heterologous antigens include, but are not limited to, bacterial, protozoan, fungal, and viral antigens. Sources of heterologous antigens include, but are not limited to, influenza virus, *helicobacter pylori, Salmonella*, rotavirus, respiratory coronavirus, etc. as described in U.S. Pat. Nos. 6,551,830, 7,432,354, and 7,339,461.

The genetically modified microorganism of the present invention can be administered in amounts and using methods that can readily be determined by persons of ordinary skill in this art. The vaccines of the present invention can be administered and formulated, for example, for oral administration, either as liquid solutions or suspensions, or solid forms suitable for solution in, or suspension in, liquid prior to administration.

Generally, the vaccine of the present invention may be administered orally in a dose effective for the production of the desired immune response. The vaccine is administered in a manner compatible with the dosage formulation, and in such amount as will be prophylactically and/or therapeutically effective. The quantity to be administered depends on the subject to be treated, the capacity of the subject's immune system to develop the desired immune response, and the degree of protection desired. Precise amounts of the vaccine to be administered in view of the subject and antigen used would be readily determined by one of skill in the art.

The genetically modified microorganism of the present invention can be formulated in a number of ways, such as encapsulated inside acid labile microcapsules, enteric coated microcapsules and capsules, polymer hydrogels, or adhesive polymer patches.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Nisin-Inducible Secretion of a Biologically Active Single-Chain Insulin Analog The following experiments were designed to explore an alternative approach to address deficiencies in prior art oral delivery systems associated with low bioavailability and to facilitate local synthesis of new therapeutic protein molecules in the small intestine. The food-grade bacterium *Lactococcus lactis* (NZ9000) was engineered for nisin-inducible expression and secretion of a bioactive single-chain insulin (SCI) analog, SCI-57. It was observed that the addition of nisin during early-log phase has a modest inhibitory effect on cell growth but induction during mid-log phase has a negligible impact on proliferation, suggesting a tradeoff between cell growth rate and duration of induction. It was observed that the signal peptide usp45 was necessary for secretion of SCI-57 into the medium. In addition, it was demonstrated that this secreted SCI-57 was biologically active, as assessed by the ability of conditioned *L. lactis* medium to stimulate Akt signaling in differentiated 3T3-L1 adipocytes. The results presented herein also show that the biological activity of SCI-57 was enhanced by near-neutral or slightly alkaline pH during induction, which is comparable to the pH in the small intestine, and by removal of a C-terminal purification tag. This study demonstrates that food-grade bacteria can be engineered to secrete bioactive insulin analogs and opens up the possibility of oral insulin delivery using live microorganisms.

The materials and methods employed in these experiments are now described.

Materials and Methods

Bacterial Strains, Plasmids and Growth Conditions

Bacterial strains and plasmids used in this work are listed in Table I. *Escherichia coli* was grown in TY medium (8 g tryptone, 5 g yeast extract and 5 g sodium chloride per liter) at 37° C. with shaking and *L. lactis* was grown in M17 medium (Oxoid, Hamshire, UK) containing 0.5% glucose (GM17) at 30° C. statically (i.e., without shaking). Solid media were prepared by adding agar (15 g per liter) to the corresponding broth. Chloramphenicol (Cm) was used at a final concentration of 10 µg/ml when culturing *E. coli* EC1000 or *L. lactis* NZ9000 harboring pNZPnisA:CYTO-LLO, pNZPnisA:SCI-57his, pNZPnisA:uspSCI-57his, or pNZPnisA:uspSCI-57.

DNA Manipulations and Transformations

Plasmid DNA from *E. coli* was isolated with a Qiagen miniprep kit (Valencia, Calif.) following the standard procedure; plasmid DNA from *L. lactis* was isolated with the same protocol except for an additional incubation of the cells with 4 mg/ml lysozyme (USB Affymetrix, Cleveland, Ohio) in P1 buffer at 37° C. for 30 min. Phusion high-fidelity DNA polymerase (NEB, Ipswich, Mass.) was used in all PCR reactions as recommended by the manufacturer. Restriction enzymes and T4 DNA ligase were purchased from NEB. DNA was transformed into *E. coli* as described previously (Pope et al., 1996, Nucleic Acids Research 24(3): 536-537). DNA was transformed into *L. lactis* by electroporation as described in the manufacturer's manual (MoBiTec, Göttingen, Germany).

TABLE I

Bacterial strains and plasmids used.

| | Characteristics | Sources |
|---|---|---|
| Strains | | |
| E. coli EC1000 | RepA+ MC1000, Km$^r$, carrying a single copy of the pWV01 repA gene in the glgB gene | (Leenhouts et al., 1996) |
| L. lactis NZ9000 | L. lactis MG1363 (nisRK genes on the chromosome) | (Kuipers et al., 1998) |
| Plasmids | | |
| pRDV:SCI-57 | pRDV containing the SCI-57 gene; Amp$^r$ | This work |
| pNZPnisA:CYTO-LLO | Modified pNZ8048 containing PnisA promoter with downstream His-tagged hly gene; Cm$^r$ | (Bahey-El-Din et al., 2008) |
| pNZPnisA:SCI-57his | Modified pNZ8048 containing PnisA promoter with downstream RGS-His-tagged SCI-57 gene; Cm$^r$ | This work |
| pNZPnisA:uspSCI-57his | Modified pNZ8048 containing PnisA promoter with downstream RGS-His-tagged SCI-57 gene; fusion with usp45 secretion leader; Cm$^r$ | This work |
| pNZPnisA:uspSCI-57 | Modified pNZ8048 containing PnisA promoter with downstream SCI-57 gene without tag; fusion with usp45 secretion leader; Cm$^r$ | This work |

Primers used for DNA amplification are listed in Table II. The gene encoding the single-chain insulin analog SCI-57 was constructed from primers 10/12 by extension PCR. Primers 11/12 were then used to amplify this SCI-57 template and the resulting product was cut with NcoI and EcoRI for ligation into the similarly cut pRDV, giving rise to pRDV:SCI-57. SCI-57 was PCR amplified from pRDV:SCI-57 using primers 1/3 and 2/3 in a preliminary step for building full constructs with and without usp45 leader sequence, respectively. The resulting PCR products were further amplified with primers 4/9 and 2/9, respectively, to add the usp45 signal and RGS-His tag or only the RGS-His tag. The PnisA promoter region was PCR amplified using primers 7/8, with 8 introducing an EcoRI site at the end of PnisA. The resulting product was fused to the SCI-57-RGS-His gene product with or without usp45 leader by assembly PCR. The assembled products were gel-purified and sequentially digested with KpnI and BglII. The digested products were then ligated into the similarly digested pNZPnisA:CYTO-LLO (plasmid courtesy of Dr. Cormac Gahan, University College Cork) using T4 DNA ligase. The ligation mixture was transformed into chemically-competent E. coli EC1000 (University of Groningen). As depicted in FIG. 1, after confirmation of the clones by DNA sequencing, the plasmids (pNZPnisA:uspSCI-57his and pNZPnisA:SCI-57) were transformed into electrocompetent L. lactis NZ9000.

TABLE II

Primers used in this study.

| Primer Number and SEQ ID NO | Primer Name | Nucleotide sequence (5'-3')$^a$ |
|---|---|---|
| 1 | SCI57_f_usp | TCCGGAGTTTACGCTTTCGTTAACCAGCAC |
| 2 | SCI57_f_nousp | CACTCAAAGAATTCATGTTCGTTAACCAGCAC |
| 3 | SCI57_r_rgshis | TGGTGGTGATGGTGGGATCCTCTGTTGCAGTAGTTTTCCA |
| 4 | usp45_f | GCACTCAAAGAATTCATGAAAAAAAAGATTATCTCAGCTATTTTAATGTCTACAGTGATACTTTCTGCTGCAGCCCCGTTGTCCGGAGTTTACGCT |
| 5 | uspSCI57_f | CCCCGTTG<u>TCCGGA</u>GTTTACGCTTTCGTTAACCAGCAC |
| 6 | stopSCI57_r_KpnI | GAACTAGT<u>GGTACC</u>TCATTAGTTGCAGTAGTTTTCC |
| 7 | PnisA_f_BglII | TACAGCTCC<u>AAGATCT</u>AGTC |
| 8 | PnisA_r_EcoRI | CAT<u>GAATTC</u>TTTGAGTGCCTCCTTATA |
| 9 | rgshis_r_KpnI | GAACTAGT<u>GGTACC</u>TCATTAATGATGGTGGTGATGGTGG |
| 10 | SCI-57gene_f | ATATAT<u>CCATGG</u>CTTCGTTAACCAGCACCTGTGCGGTTCTGACCTGGTTGAAGCTCTGTACCTGGTTTGCGGTGAACGTGGTTTCTTCTACACCGACCCGACCGGTGGTGGTCCGCGTCGTGGTATCGTTGAACAGTGCTGCCACTCTATCTGCTCTCTGTACCAGCTGGAAAACTACTGCAAC<u>GAATTC</u>GGATCTGGT |

TABLE II-continued

Primers used in this study.

| Primer Number and SEQ ID NO | Primer Name | Nucleotide sequence (5'-3')[a] |
|---|---|---|
| 11 | pRDV_f_NcoI | AGAAGGAGATATAT<u>CCATGG</u> |
| 12 | pRDV_r_EcoRI | TGGCCACCAGATCC<u>GAATTC</u> |

[a]Restriction sites are underlined.

To remove the RGS-His tag from pNZPnisA:uspSCI-57his to obtain pNZPnisA:uspSCI-57, primers 5/6 were used to PCR amplify from pRDV:SCI-57. As depicted in FIG. 1, the resulting SCI-57 gene product without the RGS-His tag was sequentially digested using KpnI and BspEI and the product was ligated into the similarly digested pNZPnisA:uspSCI-57his vector, giving rise to pNZPnisA:uspSCI-57.

Growth Curve Determination

Overnight cultures of L. lactis NZ9000(pNZPnisA:uspSCI-57his) were diluted 1:25 into fresh GM17 Cm medium. Nisin (Sigma, St. Louis, Mo.) at various concentrations was added at indicated times. Cultures were grown statically at 30° C. up to 4 hr after the latest induction point. Growth curves were determined by taking measurements of the optical density at 600 nm ($OD_{600}$) on a plate reader (Infinite M200, Tecan, Männedorf, Switzerland). The growth curves were fitted in Matlab (MathWorks, Natick, Mass.) using a logistic equation, $K/(1+e^{-r(t-1)})$, and the doubling times were calculated using $\ln(2)/r$.

Detection of Secreted SCI-57

Overnight cultures of L. lactis NZ9000(pNZPnisA:uspSCI-57his or pNZPnisA:SCI-57his) were diluted 1:25 into fresh GM17 Cm medium. For buffering with sodium phosphates, 1 M $NaH_2PO_4$ and 1 M $Na_2HPO_4$ were mixed at a molar ratio of 1:19 and added at a final concentration of 50 mM to achieve the desired pH. Cultures were grown to mid-log phase ($OD_{600} \approx 0.4$-$0.5$) for 2.5 hr and induced with 1 or 10 ng/ml nisin for 4 more hours. When investigating the effect of pH modulation, 2% or 10% culture volume of 5 N NaOH was added. At specified time points, aliquots were taken and $OD_{600}$ and pH were measured. Cells were removed from the supernatant by a 10-minute centrifugation at 4° C. and 5,000 g. The supernatant was then passed through a 0.22-µm filter (Millipore, Billerica, Mass.) to remove any cells, and 15.6 µl supernatant was mixed with reducing agent and lithium dodecyl sulfate (LDS) sample buffer (as recommended by manufacturer) for analysis by SDS-PAGE in a 12% NuPAGE® Bis-Tris gel (Invitrogen, Carlsbad, Calif.). Proteins were then transferred to a nitrocellulose membrane (Invitrogen). RGS-His-tagged proteins were analyzed by Western blotting with the RGS-His antibody (Qiagen, #34610) and then IRDye800-conjugated goat-anti-mouse immunoglobulin G secondary antibody (Rockland, Gilbertsville, Pa., #610-131-121). The blot was then scanned on an Odyssey infrared imager (LI-COR Biosciences, Lincoln, Nebr.) and the proteins were quantified by their relative intensities on the IR800 channel.

Cell Culture

The murine 3T3-L1 preadipocyte cell line (University of Pennsylvania) was maintained in Dulbecco's modified Eagle's medium (DMEM; Invitrogen) supplemented with 10% calf serum (HyClone, Logan, Utah), penicillin (100 U/ml), and streptomycin (100 µg/ml), with a change of medium every 3 days. The cells were differentiated using a slight modification of a published method (Nakashima et al., 2000, Journal of Biological Chemistry 275(17):12889-12895). Briefly, 3T3-L1 preadipocytes were allowed to grow for 2 days post-confluency and were then differentiated by addition of the same medium containing isobutylmethylxanthine (500 µM), dexamethasone (1 µM), and insulin (1 µg/ml) for 2 days and then medium containing only insulin additive for 3 additional days. The medium was then changed every 3 days until the cells contained large oil locules characteristic of fully differentiated adipocytes, typically around 9-12 days.

Bioactivity of Secreted SCI-57 on 3T3-L1 Cells

3T3-L1 preadipocytes were seeded on a 6-well plate and differentiated as described above. Fully differentiated 3T3-L1 adipocytes were serum starved overnight with 0.5% calf serum in DMEM. Supernatant of L. lactis NZ9000(pNZPnisA:uspSCI-57his or pNZPnisA:uspSCI-57) was prepared as described above. The supernatant was then concentrated 20-fold in a 3-kDa cutoff filter (Millipore) and 100 µl was added along with 2 ml DMEM to the serum-starved 3T3-L1 cells. Dilution into DMEM also ensured that all signaling assays were performed at near-neutral pH. After a 15-min incubation at 37° C., cells were washed once in PBS and lysed in cell extraction buffer (Invitrogen) supplemented with a protease inhibitor cocktail (Sigma, #P8340), phosphatase inhibitor cocktails (Sigma, #P0044 and #P5726), and phenylmethanesulfonylfluoride (Amresco, Solon, Ohio). Cell debris was removed by centrifugation at 14,000 g and 4° C. for 15 min. Cell lysate (20-50 µg, but constant for a given experiment) was mixed with reducing agent and LDS sample buffer for analysis by SDS-PAGE in a 4-12% Bis-Tris gel (Invitrogen). Proteins were then transferred to a nitrocellulose membrane. Phosphorylated Akt (p-Akt) was quantified by Western blotting, as described above, using p-Akt(Ser473) or total Akt primary antibodies (Cell Signaling Technology, Danvers, Mass., #4051 and #9272, respectively) and then IRDye800-conjugated goat-anti-mouse (same as above) or goat-anti-rabbit immunoglobulin G secondary antibody (Rockland, #611-132-122). The proteins were quantified by their relative intensities on the IR800 channel. The results of this example are now described.

Effect of Nisin Addition on L. lactis Growth Rate

Figure 2:
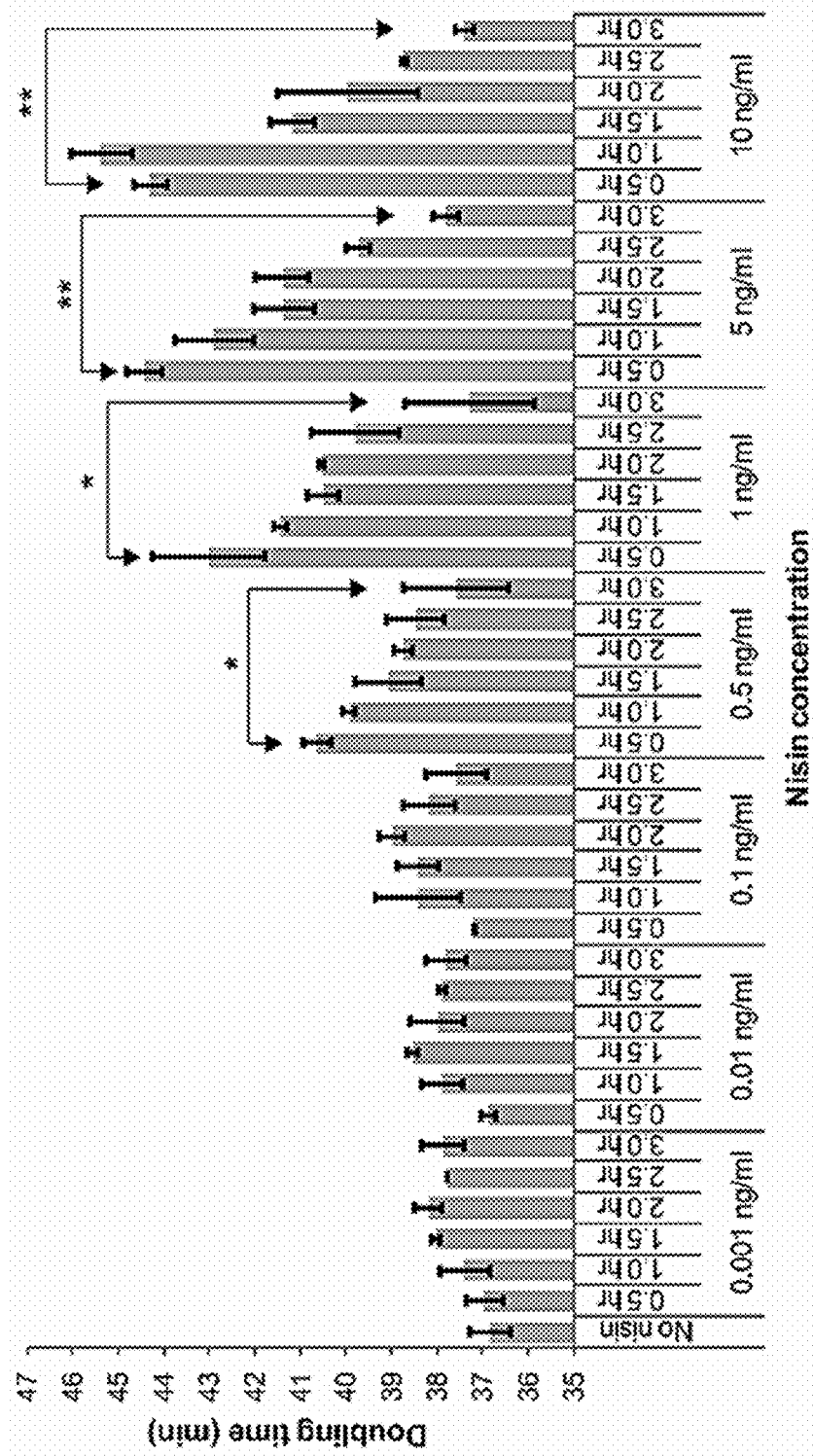
FIG. 2 depicts the results of an experiment examining the effect of nisin concentration and induction time on growth rate. Various nisin concentrations (0 to 10 ng/ml) were added at different times after 1:25 dilution of an overnight culture of NZ9000 (pNZPnisA:uspSCI-57his). Cultures were grown statically at 30° C. for a total of 7 hr. Growth was determined by measuring the optical density at 600 nm over time. The growth curves were fitted to a logistic equation $K/(1+e^{-r(t-1)})$, where r is the growth rate, and the doubling times were calculated from $\ln(2)/r$. The asterisk indicates $p<0.05$ and the double asterisks indicate $p<0.01$ for statistical comparison of doubling times after 0.5 hr and 3 hr induction at each nisin concentration using a one-tailed Student's t-test.
Figure 8:
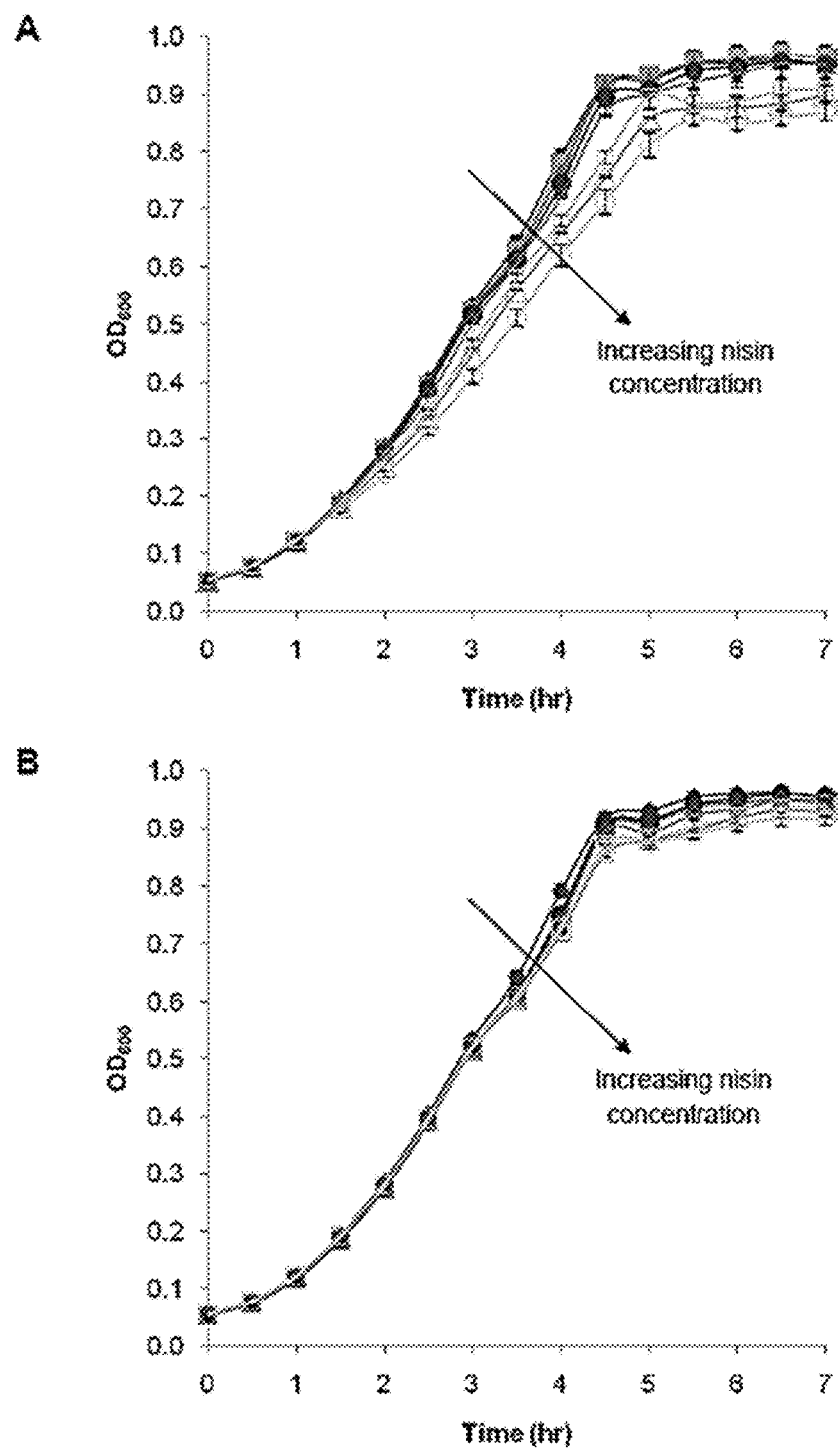
FIG. 8, comprising

The growth rate of L. lactis NZ9000 (pNZPnisA:uspSCI-57his) as a function of inducer concentration and time of induction was monitored by taking $OD_{600}$ measurements every 30 min for 7 hr. When added at 1 hr, as depicted in FIG. 8A, nisin affected cell growth in a dose-dependent manner, with the largest inhibitory effect occurring at the highest inducer concentration (10 ng/ml) (FIG. 8A). Lower $OD_{600}$ readings were observed as early as the first time point after nisin addition (within 30 min) and this attenuated signal persisted until the last time point (7 hr), indicating that nisin acted immediately and continuously on the culture until saturation. However, when the culture was induced at 2.5 hr, as depicted in FIG. 8B, lthe extent to which nisin adversely affected growth rate and saturated culture density was noticeably mitigated. Therefore a wider range of inducer concentrations (0.001, 0.01, 0.1, 0.5, 1, 5, or 10 ng/ml nisin) and induction start times (0.5, 1, 1.5, 2, 2.5, or 3 hr) were tested and as depicted in FIG. 2 the doubling time for each combination of these two variables was quantified. Low nisin concentrations (≤0.1 ng/ml) had a minimal effect on cell growth at all induction times. High nisin concentrations (≥0.5 ng/ml) resulted in significantly longer doubling times at early induction start times, but there was a clear inverse correlation between induction start time and culture doubling time.

Secretion of SCI-57 by *L. lactis* into Supernatant

Figure 3:
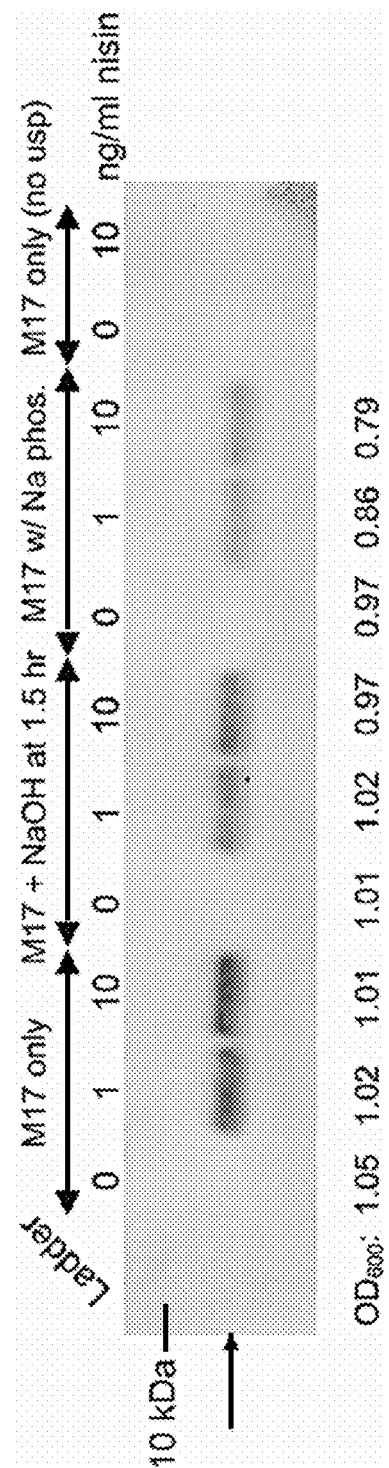
FIG. 3 depicts the results of an experiment employing a western blot to detect SCI-57 in supernatant. Overnight cultures of NZ9000(pNZPnisA:SCI-57his or pNZPnisA: uspSCI-57his) were diluted 1:25, grown in GM17 Cm media with or without 50 mM sodium phosphates for 2.5 hr, and then induced with 1 or 10 ng/ml nisin for an additional 4 hr. For modulating pH with NaOH, 10% culture volume of 5 N NaOH was added at 1.5 hr after induction. After centrifugation, the supernatant was filtered and used for Western blotting. Anti-RGS-His antibody was used to detect SCI-57 secreted into the supernatant. The molecular weight of RGS-His-tagged SCI-57, after cleavage of usp45 signal peptide, is 7.5 kDa. Arrow shows ≈7-8 kDa.

As depicted in FIG. 1B, *L. lactis* NZ9000(pNZPnisA: uspSCI-57his or pNZPnisA:SCI-57his) were grown and induced with 0, 1, or 10 ng/ml nisin at 2.5 hr as described above. As depicted in FIG. 8B and FIG. 2, the 2.5-hr induction start time was initially chosen because it seemed to balance growth rate (cultures are minimally affected even at 10 ng/ml nisin) and total induction time (SCI-57 expression can still proceed for several hours in a log-phase culture) (FIG. 8B and FIG. 2). After induction for 4 additional hours, cells were removed by centrifugation and secreted SCI-57 was detected via the C-terminal RGS-His tag using Western blotting. Bands of ≈7-8 kDa (expected: 7.5 kDa) were detected in cultures induced with 1 or 10 ng/ml nisin, while as depicted in FIG. 3, no signal was detected in the nisin-free control. This confirms that there is no detectable leaky expression from the PnisA promoter and that nisin is necessary for inducing SCI-57 expression. In addition, no signal was detected in the supernatant from *L. lactis* harboring pNZPnisA:SCI-57his (without usp45 secretion leader), whether or not nisin was added, indicating that the usp45 signal peptide is necessary for secretion of the downstream protein, which is in agreement with previous studies (Le Loir et al., 2001, Appl Environ Microbiol 67(9):4119-27; van Asseldonk et al., 1993, Mol Gen Genet 240(3):428-34). The molecular weight of RGS-His-tagged SCI-57 with the usp45 signal peptide is 10.3 kDa. As depicted in FIG. 3, all of the observed bands are below the 10 kDa mark, indicating that the usp45 signal peptide has been cleaved, as expected, from SCI-57 before or during secretion into the supernatant. Since acidification of the medium by *L. lactis* may impact cell growth and/or protein secretion, the effect of adding sodium hydroxide or sodium phosphates to GM17 media was also tested. As depicted in FIG. 3, there was no improvement in growth rate and a slight decrease in secreted SCI-57.

Bioactivity of Secreted SCI-57 on Adipocytes

To investigate if secreted SCI-57 is properly folded and biologically active, its ability to functionally signal was tested on differentiated 3T3-L1 adipocytes. Insulin signals by binding and activating cell-surface insulin receptors, which phosphorylate adapter proteins such as the insulin receptor substrate (IRS) family, which then recruit and activate downstream effector molecules. One such effector protein that is required for insulin signaling is phosphatidylinositol 3-kinase (PI 3-kinase), which phosphorylates Akt (Jiang et al., 2003, Proc Natl Acad Sci USA 100(13):7569-74; Summers et al, 1998, Mol Cell Biol 18(9): 5457-64). In the present assay, conditioned *L. lactis* medium was added to differentiated 3T3-L1 adipocytes and used p-Akt as a metric of insulin signaling. Serum-starved, fully differentiated 3T3-L1 adipocytes were incubated with 1 nM commercial insulin solution or 100 µl 20-fold-concentrated supernatant for 15 min at 37° C. and p-Akt was detected by Western blotting of cell lysates. As depicted in FIGS. 4A and 4B, both commercial insulin and supernatant from induced NZ9000(pNZPnisA:uspSCI-57his) treated with NaOH showed a strong p-Akt signal. Importantly, no signals could be seen in supernatants from uninduced NZ9000(pNZPnisA:uspSCI-57his) treated with NaOH or from induced cells without buffering or with sodium phosphate buffering, even though these latter cultures clearly secrete the full-length polypeptide as depicted in FIG. 3. These results indicate that functional folding of secreted SCI-57 is an important bottleneck in obtaining bioactive product from *L. lactis*, but this bottleneck is dependent on the pH and buffer conditions in the medium. To estimate the concentration of active RGS-His-tagged SCI-57 in the supernatant, we quantified p-Akt signals from the Western blots of three independent experiments and found the signal of SCI-57 to be roughly equivalent to 1 nM commercial insulin (FIG. 4B). Since 100 µl of 20-fold-concentrated supernatant was added to 2 ml DMEM, the original concentration of functional SCI-57 secreted by NZ9000(pNZPnisA:uspSCI-57his) was approximately 1 nM.

Effect of pH Modulation on Functional SCI-57 Expression

Figure 4:
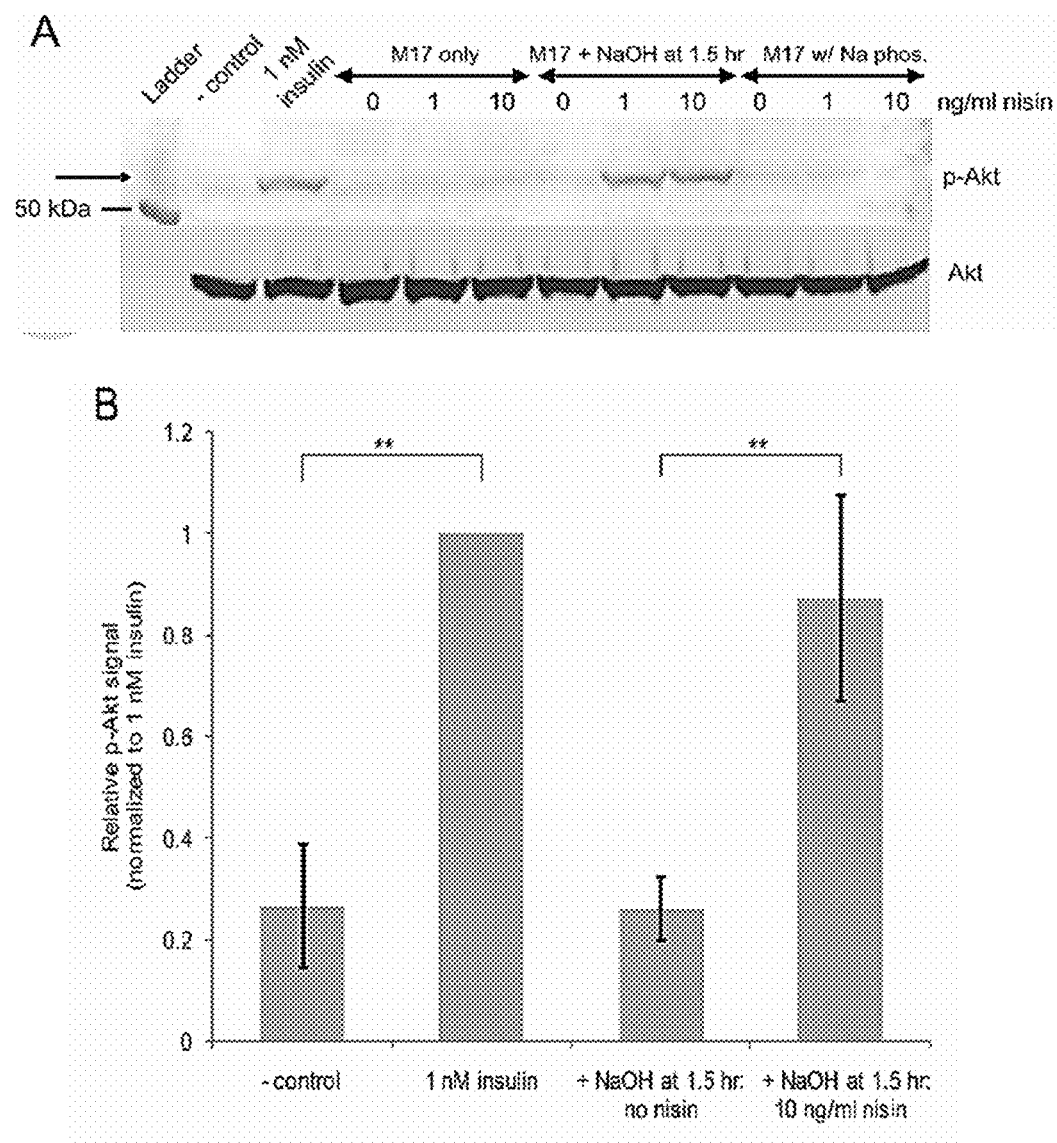
FIG. 4 depicts the results of an experiment evaluating in vitro biological activity of secreted SCI-57. (A) Representative blot of p-Akt signaling. Supernatant of NZ9000 (pNZPnisA:uspSCI-57his or pNZPnisA:uspSCI-57) cultures were prepared as described in FIG. 3, and were then concentrated 20-fold with a 3-kDa cutoff filter. Concentrated supernatant (100 μl) was added to 2 ml DMEM on fully differentiated, serum-starved 3T3-L1 adipocytes. After a 15-min incubation at 37° C., cells were lysed and the lysates were blotted for p-Akt(Ser473). (B) Quantification of p-Akt signaling from 3 independent experiments. Relative intensities are shown by normalizing to the positive control (1 nM commercial insulin). Double asterisks indicate $p<0.01$.
Figure 5:
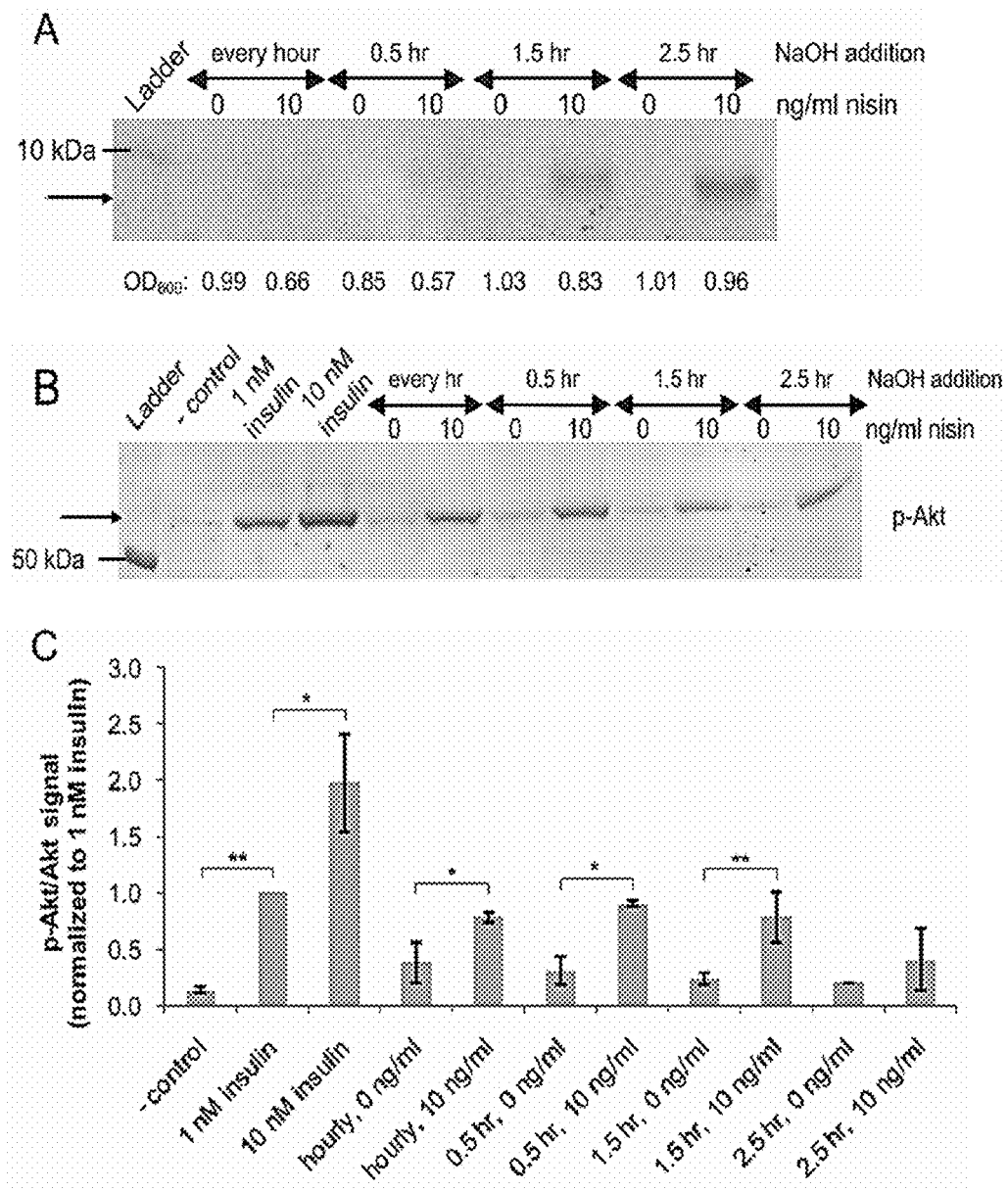
FIG. 5 depicts an experiment evaluating the effect of temporal pH modulation on SCI-57 secretion and bioactivity. (A) Western blot showing secreted SCI-57 with different NaOH treatments, with final $OD_{600}$ readings given below. Overnight cultures of NZ9000(pNZPnisA:uspSCI-57his) were diluted 1:25 and grown in GM17 Cm media for 2.5 hr and induced with 0 or 10 ng/ml nisin for an additional 4 hr. For continuous pH regulation with NaOH, 2% culture volume of 5 N NaOH was added at 1.5, 2.5, 3.5, 4.5, and 5.5 hr after the 1:25 dilution. For single-dose modulation with NaOH, 10% culture volume of 5 N NaOH was added at 0.5, 1.5, or 2.5 hr after nisin induction. After centrifugation, the supernatant was filtered and used directly for Western blotting. RGS-His antibody was used to detect the RGS-His-tagged SCI-57 secreted into the supernatant. (B) Representative Western blot showing relative p-Akt signals on differentiated 3T3-L1 adipocytes stimulated by supernatant in different buffering conditions. Supernatant of NZ9000 (pNZPnisA:uspSCI-57his) culture was prepared as described in FIG. 5A, concentrated 20-fold, and 100 μl was added along with 2 ml DMEM to 3T3-L1 cells. After a 15-minute incubation at 37° C., cells were lysed and the lysate subjected to Western blotting and detection with a p-Akt antibody. (C) Quantification of p-Akt signals, as shown in (B), from two independent experiments. Notation for the last eight samples is: NaOH addition time after nisin induction, nisin concentration. Asterisk indicates $p<0.05$ and double asterisks indicate $p<0.01$.

The previous results, as depicted in FIGS. 3 and 4, indicate that the biological activity of SCI-57 is more heavily affected by the medium pH and buffering conditions than by the overall protein secretion level. We therefore investigated the biological activity of various conditioned *L. lactis* media, each subject to a different pH profile, on 3T3-L1 adipocytes. Two modes of pH modulation were tested: 1) continuous control, in which 2% culture volume of 5 N NaOH was added hourly for 5 hours; or 2) a single pulse, in which 10% culture volume of 5 N NaOH was added once at the indicated time after induction. In effect, the same total amount of NaOH was added in each case. As seen from the $OD_{600}$ readings, as depicted in FIG. 5A, early addition of NaOH (continuous or single dose at 0.5 hr) has an inhibitory effect on growth. Corresponding to the lower $OD_{600}$ readings, the amount of secreted SCI-57 detected for culture with early NaOH addition was also lower on a per-volume basis. However, as depicted in FIG. 5B, when the biological activity of these samples was tested using our p-Akt signaling assay on 3T3-L1 adipocytes, the observed trend was the opposite of that seen in FIG. 5A. Cultures grown with early NaOH addition secrete similar, if not higher, levels of functional SCI-57 than cultures grown with late NaOH addition. This further confirms that the biological activity of secreted SCI-57 is more heavily affected by buffering conditions than total secretion level and suggests that earlier counterbalancing of the natural medium acidification increases the fraction of functional SCI-57 molecules.

Further Enhancement of SCI-57 Bioactivity by Removal of RGS-his Tag

Figure 6:
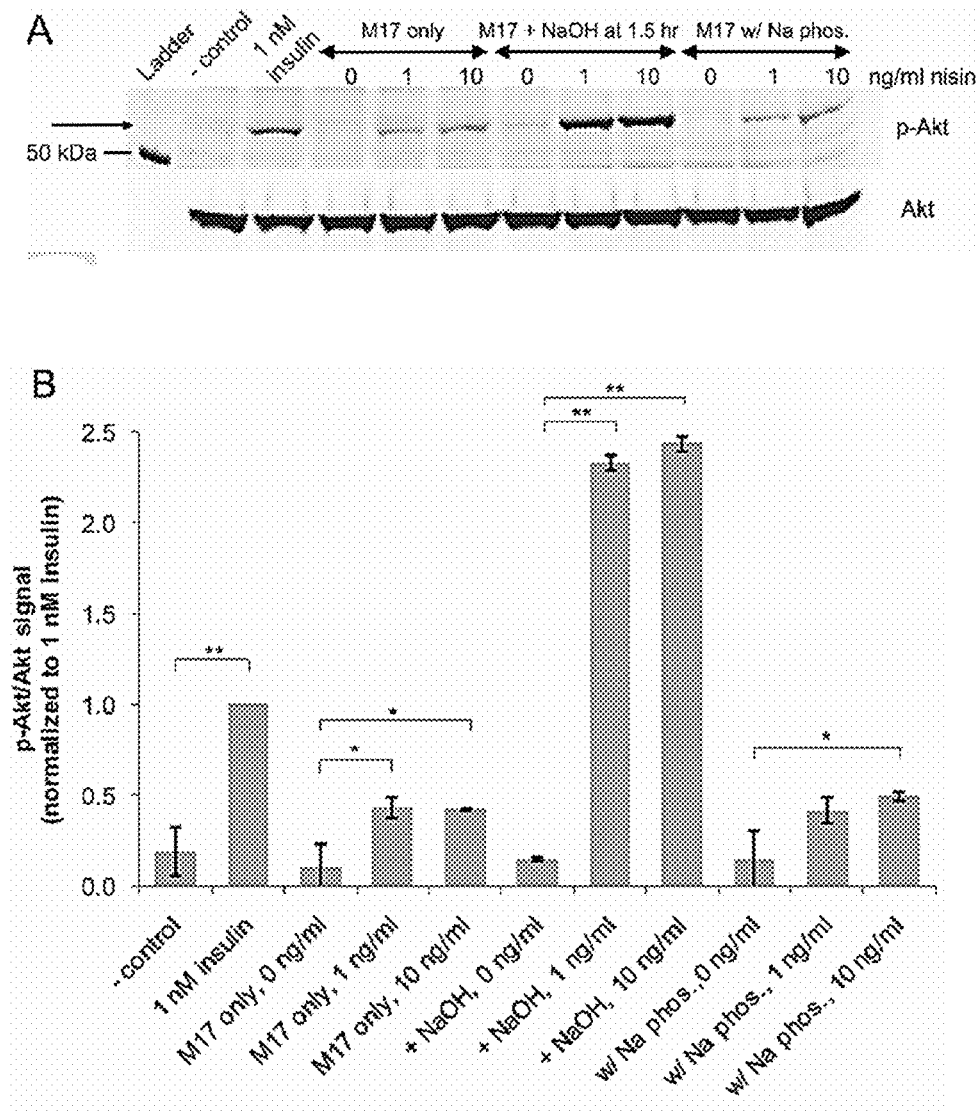
FIG. 6 depicts an experiment evaluating the biological activity of secreted SCI-57 without the RGS-His tag. (A) Representative Western blot showing relative p-Akt signals on differentiated 3T3-L1 adipocytes stimulated by supernatant from NZ9000 (pNZPnisA:uspSCI-57 (no RGS-His tag)) cultures. Supernatants were prepared as described in FIG. 3 and signaling experiments were carried out as described in FIG. 4A. (B) Quantification of p-Akt signals, as shown in (A), from 2 independent experiments. Notation for the last nine samples is: medium composition, nisin concentration. Asterisk indicates $p<0.05$ and double asterisks indicate $p<0.01$.

Finally, it was investigated whether the addition of the RGS-His tag, which is convenient for detection and assay development but not desirable for eventual in vivo applications, has any effect on the bioactivity of SCI-57. The p-Akt signaling experiments on 3T3-L1 adipocytes were therefore repeated with conditioned media from NZ9000(pNZPnisA: uspSCI-57) cultures. As depicted in FIG. 6, not only was p-Akt signaling much stronger for cultures treated with NaOH but it was now also detectable using untreated cultures or cultures with phosphate buffer. This suggests that the RGS-His tag adversely affects insulin receptor binding and/or SCI-57 folding.

Food-Grade Microorganisms Engineered to Secrete Bioactive Insulin Analogs

As depicted in FIG. 2, both nisin concentration and time of induction affect the growth rate. For a given induction time, a higher nisin concentration increases the doubling time (i.e., slows the growth rate). This is possibly due to a combination of increased burden from producing heterologous protein and nisin toxicity (nisin can inhibit bacterial cell wall biosynthesis and can kill cells by forming pores in the cytoplasmic membrane (McAuliffe et al., 2001, FEMS Microbiol Rev 25(3):285-308). For a given nisin concentration, a later induction time reduces the doubling time (i.e., increases the growth rate). There is perhaps a critical $OD_{600}$ threshold in early- to mid-log phase above which the burdens imposed by heterologous protein synthesis and nisin toxicity are offset by the faster growth rate in this phase.

TABLE III pH values during different induction conditions.

| | Starting pH | Ending pH | pH Spike | Insulin activity[a] (with RGS-His tag) | Insulin activity[a] (no tag) |
|---|---|---|---|---|---|
| M17 only | 6.9 | 5.7 | no | − | + |
| M17 with 50 mM sodium phosphates | 7.2 | 6.5 | no | − | + |
| M17 with NaOH addition every hour | 6.9 | 7 to 7.7 | no | ++ | N.D. |
| M17 with NaOH addition at 0.5 hr | 6.9 | 7 to 9.17 | >9 | ++ | N.D. |
| M17 with NaOH addition at 1.5 hr | 6.9 | 6.9 to 7.1 | >7.7 | ++ | +++ |
| M17 with NaOH addition at 2.5 hr | 6.9 | 7.2 to 7.7 | >7.7 | + | N.D. |

[a]−: no activity; +: equivalent to <1 nM commercial insulin; ++: equivalent to ≈1 nM commercial insulin; +++: equivalent to >1 nM commercial insulin; N.D.: not determined The correlation between pH regulation and SCI-57 bioactivity is summarized in Table III. *L. lactis* naturally acidifies the GM17 medium to pH<5.7 when the culture is saturated. Regulating the pH with a base or buffering the media allows *L. lactis* to grow to a much higher density (Tremillon et al., 2010, Microbial Cell Factories 9:37) and it has also been shown to increase the stability and biological activity of secreted interleukin-10 (Schotte et al., 2000, Enzyme Microb Technol 27(10):761-765). In the present experiment, buffering the medium may increase the solubility, stability, and/or folding of secreted SCI-57. SCI-57 has a pI similar to native insulin and is most soluble at neutral pH (Hua et al., 2008, Journal of Biological Chemistry 283(21):14703-16). Also, wild-type insulin is most stable near neutral pH, due to deamidation at low pH and aggregation at high pH (Brange et al., 1992, Acta Pharm Nord 4(3):149-58). However, since the pH during our induction experiments stays relatively close to neutral pH, deamidation and aggregation are unlikely to have large effects. Furthermore, SCI-57 was designed with amino acid substitutions in the A and B chains to prevent dimerization and higher order assembly (Hua et al., 2008, Journal of Biological Chemistry 283(21):14703-16). Thus, it possible that the marked increase in biological activity upon addition of NaOH is primarily due to better folding. SCI-57, like native insulin, requires 3 disulfide bonds (A6-A11, A7-B7, A20-B19) for correct folding and biological activity. Previous work indicated that basic pH facilitates folding of insulin by deprotonating thiolate moieties and thus limiting aggregation of reduced B chains, giving rise to more free B chains that can form productive disulfide bonds with A chains (Hua et al., 2002, Journal of Biological Chemistry 277(45):43443-53; Weiss, 2009, Journal of Biological Chemistry 284(29): 19159-63). Also, thiol-disulfide exchange, the principal mechanism by which disulfide bonds are formed and rearranged in proteins, proceeds via a nucleophilic attack of the thiolate anion and alkaline conditions facilitate this reaction (Rudolph et al., 1996, FASEB J 10(1):49-56). In the present experiment, the addition of NaOH could provide a transient alkaline environment to more efficiently facilitate formation of the disulfide bonds of SCI-57, thus giving rise to higher biological activity. During the folding of insulin, there exists a critical folding intermediate containing the single disulfide A20-B19, which has been suggested to form first and guide subsequent folding (Yan et al., 2003, Protein Sci 12(4):768-75). The posited initial formation of this disulfide bond may also explain why SCI-57 without the RGS-His tag exhibits higher biological activity even without pH modulation. The RGS-His tag in our experiments is fused directly to the C-terminus of SCI-57 (i.e., after A21), which might impede the formation of this initial disulfide bond.

The experiments presented herein demonstrate proof of principle that food-grade microorganisms can be engineered to secrete bioactive insulin analogs. One notable difference between the in vitro experiments presented here and the actual in vivo environment is the pH-sensitive bioactivity. While pH decreases in the current experiments significantly hindered the bioactivity (e.g., without intervention with NaOH), the gut is highly pH-regulated and will not be affected by the acidification that occurs in unbuffered M17 medium in vitro. Furthermore, *L. lactis* resides in the jejunum and ileum of human intestine (Wells et al., 2008, Nat Rev Microbiol 6:349-62), which have pH values of ~6.2 and ~6.8-8.4, respectively (Charman et al., 1997, J Pharm Sci 86(3):269-82). These pH values were closely approximated in the experiments in which functional SCI-57 was observed. In addition, SCI-57 administered in vivo will not have an RGS-His tag, elimination of which should substantially increase the biological activity of the protein. Additionally, to avoid potential complications with induction in vivo, it may be possible to preinduce *L. lactis* with nisin prior to oral administration. For example, it has been previously shown that treating *L. lactis* with a 1-hour pulse of nisin can induce protein secretion for 10 hours (Bermudez-Humaran et al., 2003, FEMS Microbiol Lett 224(2):307-13).

In summary, a *L. lactis* strain has been constructed. This *L. lactis* strain can efficiently secrete SCI-57 that is biologically active at the physiological pH in the gut. From a biomedical perspective, the advantages of this system for oral insulin delivery are threefold. First, *L. lactis* has long been shown to have a safe association with humans, and thus possible adverse effects, as compared with other delivery systems, can be minimized Second, the protein can by secreted locally in the small intestine, minimizing loss during passage through the upper digestive tract, as compared with other delivery systems, and enabling 'on demand' secretion. Third, as a live delivery vehicle, the pharmacokinetics can be genetically tuned to match delivery requirements. From a biotechnological perspective, using SCI-57-secreting *L. lactis* eliminates the needs for two-chain synthesis, expensive protein purification, and temperature-sensitive storage of insulin, offering a cheaper and more convenient alternative to traditional insulin replacement therapy.

Figure 7:
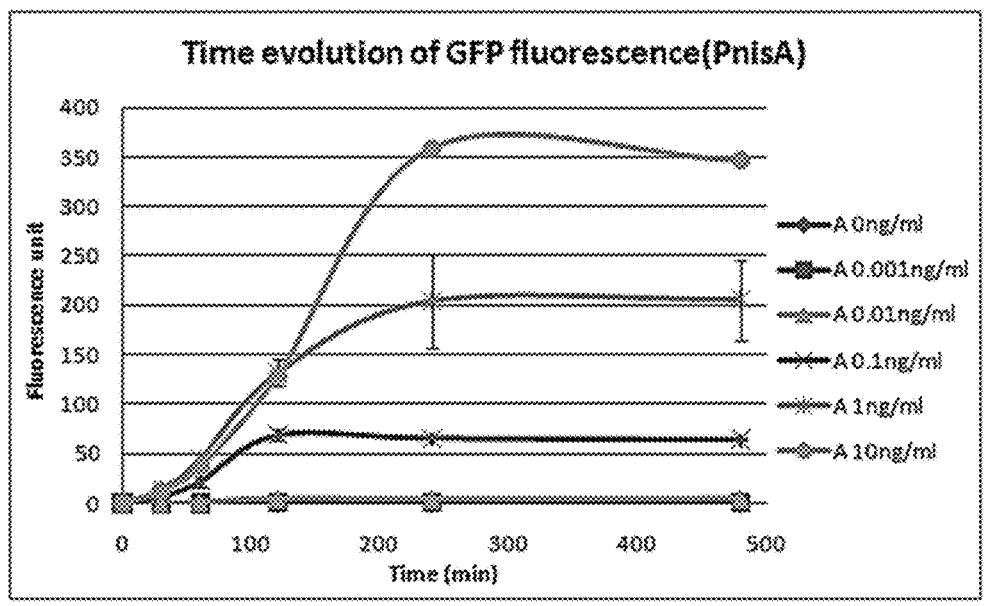
FIG. 7 depicts an experiment evaluating the (A) Kinetics of GFP expression using PnisA for a range of nisin concentrations (0.001-10 ng/ml). (B) Steady-state GFP response with PnisA and PnisF promoters for the same range of nisin concentrations. The background-subtracted GFP signal at 10 ng/ml nisin is ~350 using PnisA and ~15 using PnisF.
Figure 7:
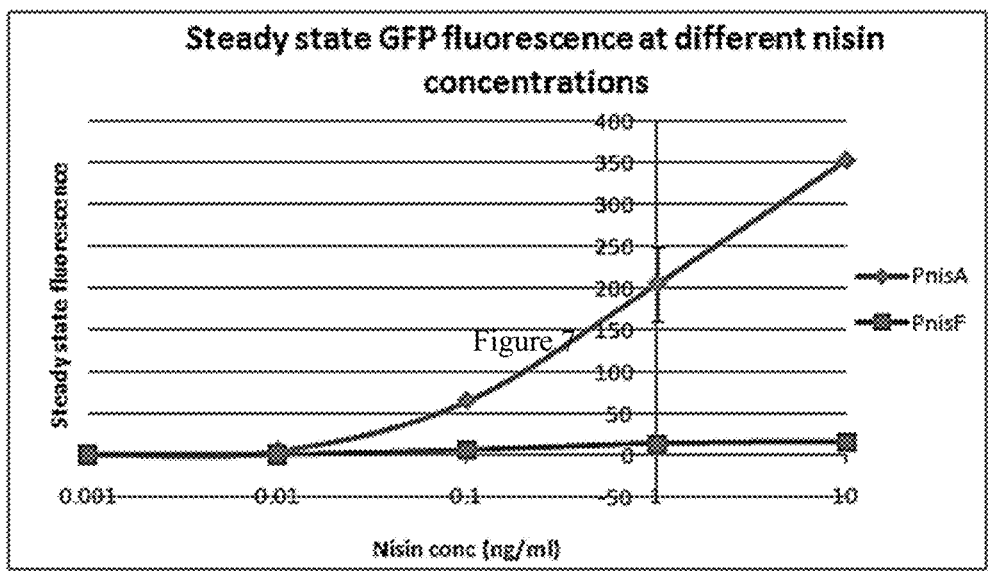

Example 2: Engineered Bacteria for Oral Delivery of Glucoregulatory Proteins It has been demonstrated, as depicted in FIG. 7, that the expression level of green fluorescent protein (GFP) in the *L. lactis* strain NZ9000 using plasmid pNZ8048 (de Ruyter et al., 1996, Appl Environ Microbiol 62:3662-3667) can be tuned by at least two different nisin-inducible promoters, $P_{nisA}$ and $P_{nisF}$. (de Ruyter et al., 1996, J Bacteriol 178: 3434-3439). Furthermore, replacement of the GFP gene with that for a single-chain insulin, SCI-57, preceded by a usp45 leader sequence (van Asseldonk et al., 1990, Gene 95:155-160) for protein secretion results in secretion of intact SCI-57 protein into the supernatant. The ability of *L. lactis*-secreted SCI-57 to signal on 3T3-L1 cells also has been characterized and it is found that induced *L. lactis* (but not uninduced *L. lactis*) could induce Akt signaling.

The topology of the synthetic circuit is inspired by both the computational work (Palani et al., 2008, Biophys J 95:1575-1589; Palani et al., 2009, PLoS Comp Biol 5, e1000518) and the experimental work. The present computational studies of lineage commitment in hematopoiesis suggested that the two-positive feedback mechanism can generate robust ultrasensitivity and reversible bistability. The potential generalizable utility of this network is intriguing because it enables the conversion of any graded receptor-mediated signal into a tunable, reversible switch. This robustness in a completely artificial signaling network in *Saccharomyces cerevisiae* (also using *Arabidopsis* signaling components in this host (Chen et al., 2005, Nat Biotechnol 23:1551-1555)) has been tested. The original network and receptor-only feedback networks are graded. The transcription-only feedback network is slightly ultrasensitive. The two-feedback network is highly ultrasensitive and also bistable. This simple network can also be tuned simply by changing these two promoter strengths to change useful system behaviors, including the steady-state amplitude, the activation kinetics, and the deactivation kinetics. Here, the experiments were designed to construct the same topology in *L. lactis* by reworking the NisK/NisR signaling pathway. For therapeutic purposes, the activation and deactivation kinetics can be decoupled by ingesting pre-induced *L. lactis*; in this way, the timescale for therapeutic protein expression (corresponding to deactivation kinetics) can be tuned without regard to the activation kinetics.

Example 3: Activities of *L. lactis*-Produced Single-Chain Insulin (SCI), Leptin, and SCI-Leptin Fusion In Vitro and In Vivo SCI, leptin, and SCI-leptin fusions are express in *L. lactis* and bioactivity is tested in vitro. As noted in Example 2, *L. lactis* secreting SCI-57 were successfully engineered and the product appears to be bioactive. To further evaluate this bioactivity, other insulin signaling molecules are probed using differentiated 3T3-L1 cells. Cell lysates are immunoprecipitated with antibodies against insulin receptor substrates (IRS1 or IRS2) (Santa Cruz Biotechnology), and immunoblotting is done using antibodies against phospho-IRS1, phosphatidylinositol 3-kinase (PI3K) p85 subunit (Santa Cruz Biotechnology), and pY-4G10 (Upstate Biotechnology) to detect IRS2.

Human leptin (cDNA from Origene, #SC120021) is expressed using the expression vector (pNZ8048), the leader sequence (usp45), the *L. lactis* strain (NZ9000), and the medium (M17). Leptin expression is determined by Western blot (via RGS-His tag) and ELISA (Peprotech, #900-K90). Leptin activity is measured using a luminescence assay with leptin receptor-transfected HEK-293 cells and looking at STAT-3 responsive firefly luciferase signals (Yang et al., 2004, Mol Endocrinol 18:1354-1362).

Several fusions of SCI-57 and leptin are constructed to test for functional expression. Since it has been shown that SCI-57 retains activity at the N-terminus of a fusion, and since leptin has been shown to retain activity at the C-terminus of a fusion (Lo et al., 2005, Protein Eng Des Sel 18:1-10), at least one of the fusions is designed in a SCI-57-linker-leptin configuration. The amino acid linkers included in various fusions of the invention include: GGSG (short; SEQ ID NO:13), GAGGSGGS (medium; SEQ ID NO:14), GGGSGGAGGGSG (long; SEQ ID NO:15), AEAAAKEAAAKA (helix-forming; SEQ ID NO:16) (Arai et al., 2001, Protein Eng 14:529-532), GSPDGDIDGS (trypsin and chymotrypsin resistant; SEQ ID NO:17), and GSLVPRGSGS (thrombin-cleavable; SEQ ID NO:18) (Chang, 1985, Eur J Biochem 151:217-224). In further embodiments, the length of these linkers is extended to ensure adequate linker length for proper folding of the fusions. Protein expression is determined by Western blotting and activity of the fusions is tested in both insulin and leptin signaling assays, as described elsewhere herein.

Example 4: Engineered *L. Lactis* to Diabetic Mice and In Vivo Pharmacokinetic and Pharmacodynamic Parameters are Measured To generate diabetic mice, 10 week old male C57BL/6J mice (Jackson Laboratory) are injected with streptozotocin (50 mg/kg in 0.1 mol/L citrate buffer, pH 4.0) intraperitoneally (i.p.) daily for 5 days (Like et al., 1976, Science 193:415-417). Control mice receive citrate buffer i.p. for 5 days. Tail blood glucose is measured daily after treatment. The induction of diabetes is defined as tail blood glucose level greater than 250 mg/dl, measured with a glucometer (e.g., One Touch Ultra II) following 6 hours of short fast. Generally, more than 90% of streptozotocin-treated mice develop diabetes within 2 weeks.

Diabetic mice are fasted for 6 hours and tail glucose is measured with a glucometer. Saline buffer, recombinant human insulin (10-50 U/kg dose; Novo Nordisk), recombinant human leptin (1-5 U/kg dose; Amylin Pharmaceuticals), pre-induced *L. lactis* with no construct ($10^9$-$10^{10}$ CFU), pre-induced *L. lactis* engineered to express the SCI-57 construct ($10^9$-$10^{10}$ CFU), pre-induced *L. lactis* engineered to express the leptin construct ($10^9$-$10^{10}$ CFU), and pre-induced *L. lactis* engineered to express the various fusion constructs of the invention as elsewhere described herein ($10^9$-$10^{10}$ CFU) are administered via oral gavage (n=5/treatment/dose; $n_{total}$=65). Tail blood glucose is measured after 30 min and 1 hour and then hourly for 6 hours.

To determine the pharmacokinetics of therapeutic protein delivery, either pure protein or at least one of the engineered *L. lactis* strains of the invention is administered to diabetic mice via oral gavage. Groups of mice (e.g., n=5) are euthanized 30 min and 1, 2, 3, 4, 5, and 6 hours after treatment. Serum is harvested for measurement of the insulin analog, leptin analog, and or fusion protein. To assess pharmacodynamics, liver samples are harvested and frozen in liquid nitrogen for immunoblotting of insulin and leptin signaling molecules, as described elsewhere herein.

Glucose and insulin tolerance testing is performed to screen for abnormal glucose metabolism. For glucose tolerance, mice are fasted in their home animal facilities overnight prior to oral lavage of saline buffer, recombinant human insulin (Novo Nordisk), recombinant human leptin (Amylin Pharmaceuticals), *L. lactis* with no construct, *L. lactis* engineered to express the SCI-57 construct, *L. lactis* engineered to express the leptin construct, and *L. lactis* engineered to express the various fusion constructs of the invention as elsewhere described herein (e.g., n=5/treatment). Glucose (2 g/kg i.p.) is then injected to all groups. Water is provided during overnight fast and throughout the glucose tolerance testing. The same mice used for glucose tolerance testing are allowed to recover for 1 week in their home cages in the animal facility, and then undergo insulin tolerance testing. For insulin tolerance, mice are subjected to a morning fast prior to oral gavage of saline buffer, recombinant human insulin (10-50 U/kg dose; Novo Nordisk), recombinant human leptin (1-5 U/kg dose; Amylin Pharmaceuticals), *L. lactis* with no construct ($10^9$-$10^{10}$ CFU), *L. lactis* with SCI-57 construct, *L. lactis* with leptin construct, and *L. lactis* with the best fusion construct from in vitro analysis above. Water is provided during the fast and testing. Tail blood (2 µl) is collected at baseline and 15, 30, 60, and 120 minutes following injection of glucose or insulin, for measurement of glucose by glucometer.

Alternatively, codon optimization of the leptin gene (Le Loir et al., 2001, Appl Environ Microbiol 67:4119-4127) can be performed and/or known stabilizing mutations that retain bioactivity (Zhang et al., 1997, Nature 387:206-209) can be introduced. These optimizations can also be applied to the fusion proteins. The existing experimental evidence suggests that the experiments can be conducted by using SCI-linker-leptin fusions configuration, alternatively, by using leptin-linker-SCI fusions.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A genetically modified microorganism for oral delivery of a therapeutic glucoregulatory protein to a mammal, wherein said microorganism comprises a nucleic acid molecule encoding said therapeutic glucoregulatory protein, wherein said microorganism produces said therapeutic glucoregulatory protein and secretes said therapeutic glucoregulatory protein in the intestine of the mammal, wherein said therapeutic glucoregulatory protein is a fusion protein comprising insulin and leptin, and wherein the leptin of the fusion protein is able to facilitate passing of the fusion protein across the intestinal lumen and into the circulation.

2. The microorganism of claim 1, wherein said microorganism is a gram positive bacterium.

3. The microorganism of claim 2, wherein said microorganism is *Lactococcus lactis*.

4. The microorganism of claim 3, wherein said *Lactococcus lactis* is the NZ9000 strain, further wherein said microorganism has been engineered for nisin-inducible expression and secretion of said therapeutic glucoregulatory protein.

* * * * *